(12) United States Patent
Knopp et al.

(10) Patent No.: US 6,830,450 B2
(45) Date of Patent: Dec. 14, 2004

(54) SYSTEMS AND METHODS FOR IMPROVED ENGAGEMENT BETWEEN ALIGNERS AND TEETH

(75) Inventors: Peter G. Knopp, Palo Alto, CA (US); Aaron J. Miller, San Francisco, CA (US); Rob Van Den Berg, San Ramon, CA (US)

(73) Assignee: Align Technology, Inc., Santa Clara, CA (US)

( * ) Notice: Subject to any disclaimer, the term of this patent is extended or adjusted under 35 U.S.C. 154(b) by 122 days.

(21) Appl. No.: 10/126,105

(22) Filed: Apr. 18, 2002

(65) Prior Publication Data

US 2003/0198911 A1 Oct. 23, 2003

(51) Int. Cl.[7] .................................................. A61C 3/00
(52) U.S. Cl. ................................ 433/6; 433/24; 433/18
(58) Field of Search ................................ 433/6, 18, 24, 433/215

(56) References Cited

U.S. PATENT DOCUMENTS

| | | |
|---|---|---|
| 3,407,500 A | 10/1968 | Kesling |
| 3,660,900 A | 5/1972 | Andrews |
| 4,020,558 A | 5/1977 | Cournut et al. |

(List continued on next page.)

FOREIGN PATENT DOCUMENTS

| | | |
|---|---|---|
| DE | 4020647 A1 | 6/1990 |
| EP | 1108397 A1 | 12/2000 |
| FR | 2 369 828 | 7/1978 |
| WO | WO 98/58596 A1 | 12/1998 |

OTHER PUBLICATIONS

Boughton, B., Invisible Force, *ContactPoint*, University of the Pacific School of Dentistry, San Francisco, California, 80(3) pp. 21–24 (2000).

Chiappone, Constructing the Gnathologic Setup and Positioner, *J. Clin. Orthod.* 14:121–133 (1980).

Cottingham, Gnathologic clear plastic positioner, *Am. J. Orthodontics* 55:23–31 (1960).

Cureton, Correcting Malaligned Mandibular Incisors with Removable Retainers, *J. Clin. Orthodon.* 30:390–395 (1996).

Doyle, Digital Dentistry, *Computer Graphics World* Oct. 2000, pp. 51–54.

(List continued on next page.)

*Primary Examiner*—Todd E. Manahan
(74) *Attorney, Agent, or Firm*—Townsend and Townsend and Crew LLP; Bao Tran, Esq.

(57) ABSTRACT

A system and method for repositioning teeth in a patient jaw includes an attachment bonded to a tooth. The attachment has at least one force receiving component for receiving a force. A polymeric shell repositioning appliance is positioned over at least some of the teeth in the patient jaw. The polymeric shell has at least one force transmitting component for engaging the force receiving component to form a locus of engagement. The locus of engagement transmits the force and moves but is maintained as the tooth is repositioned. In specific embodiments the locus of engagement is maintained over a substantial range of motion. The force transmitted at the locus of engagement increases in response to the tooth lagging an intended position. A space between the positioned appliance and the tooth permits the tooth to move into an intended position.

56 Claims, 25 Drawing Sheets

U.S. PATENT DOCUMENTS

| | | |
|---|---|---|
| 4,253,828 A | 3/1981 | Coles et al. |
| 4,504,225 A | 3/1985 | Yoshii |
| 4,505,673 A | 3/1985 | Yoshii |
| 4,591,341 A | 5/1986 | Andrews |
| 4,609,349 A | 9/1986 | Cain |
| 4,664,626 A | 5/1987 | Kesling |
| 4,676,747 A | 6/1987 | Kesling |
| 4,755,139 A | 7/1988 | Abbatte et al. |
| 4,793,803 A | 12/1988 | Martz |
| 4,798,534 A | 1/1989 | Breads |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,983,334 A | 1/1991 | Adell |
| 5,022,855 A | 6/1991 | Jeckel |
| 5,035,613 A | 7/1991 | Breads et al. |
| 5,049,077 A | 9/1991 | Goldin et al. |
| 5,055,039 A | 10/1991 | Abbatte et al. |
| 5,059,118 A | 10/1991 | Breads et al. |
| 5,125,832 A | 6/1992 | Kesling |
| 5,145,364 A | 9/1992 | Martz et al. |
| 5,186,623 A | 2/1993 | Breads et al. |
| 5,536,168 A | 7/1996 | Bourke |
| 5,542,842 A | 8/1996 | Andreiko et al. |
| 5,607,300 A | 3/1997 | Tepper |
| 5,645,420 A | 7/1997 | Bergersen |
| 5,683,244 A | 11/1997 | Truax |
| 5,692,894 A | 12/1997 | Schwartz et al. |
| 5,964,587 A | 10/1999 | Sato |
| 5,975,893 A | 11/1999 | Chishti et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,227,850 B1 | 5/2001 | Chishti et al. |
| 6,257,882 B1 | 7/2001 | Wyllie, II |
| 6,276,930 B1 | 8/2001 | Pozzi |
| 6,299,440 B1 | 10/2001 | Phan et al. |
| 6,309,215 B1 | 10/2001 | Phan et al. |

OTHER PUBLICATIONS

Elsasser, Some Observations on the History and Uses of the Kesling Positioner, *Am. J. Ortho.* 36:5, (May 1950).

Friedman (Ed.) Technology Forum, Compendium:22(2), (Feb. 2001).

Kamada et al. Case Reports on Tooth Positioners using LTV Vinyl Silicone Rubber, *J. Nihon Univ. School of Dentistry* 26(1), 11–29 (Mar. 1984).

Kamada et al., Construction of Tooth Positioners with LTV Vinyl Silicone Rubber and Some Case Reports, *J. Nihon Univ. School of Dentistry*, 24(1):1–27 (Mar. 1982).

Kessling, The Philosophy of the Tooth Positioning Appliance, *Am. J. Orthod Oral Surg.*, 31:297–304, (1945).

Kesling, Coordinating the Predetermined Pattern and Tooth Positioner with Conventional Treatment, *Am. J. Orthod. Oral Surg.*. 32:285–293, (1946).

Kleeman et al., The Speed Positioner, *J. Clin. Orthod.* 30:673–680, (1996).

Yoshii, Research on a New Orthodontic Appliance: The Dynamic Positioner (D.P.), *Nippon Dental Review* 452: 61–74 (1980).

Yoshii, Research on a New Orthodontic Appliance: The Dynamic Positioner (D.P.), *Nippon Dental Review* 454: 107–130 (1980).

Yoshii, Research on a New Orthodontic Appliance: The Dynamic Positioner (D.P.), *Nippon Dental Review* 457:146–164 (1980).

Yoshii, Research on a New Orthodontic Appliance: The Dynamic Positioner (D.P.), *Nippon Dental Review* 458:112–129 (1980).

New Orthodontic Device–Dynamic Positioner (D.P.)—Ill Case Reports of Reversed Occlusion, *Nippon Dent. Res.* 457:146–164 (1980).

Nishiyama et al., A New Construction of Tooth Positioner by LTV Vinyl Silicone Rubber, *J. Nihon Univ. School of Dentistry*, 19:93–102 (1977).

Shilliday, Minimizing finishing problems with the mini–positioner, *Am. J. Orthodontics* 59:596–599 (1971).

Warunek, et al., Physical and mechanical properties of elastomers in orthodontic positioners, *Am. J. Orthod. Dentofac. Orthop.*, 95(5): 388–400 ((19889).

Warunek, et al., Clinical Use of Silicone Elastomer Appliances, *JCO Inc.* 1989.

Wells, Application of the positioner appliance in orthodontic treatment, *Am. J. Orthodont.* 58:351–366 (1970).

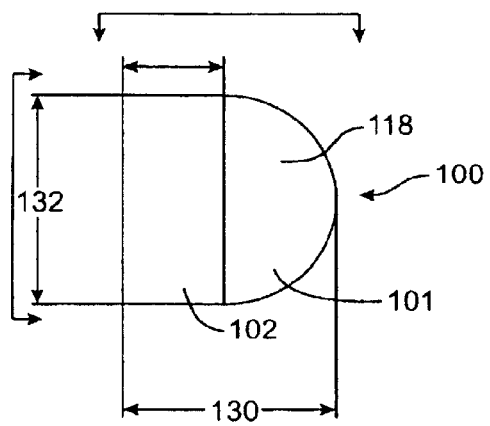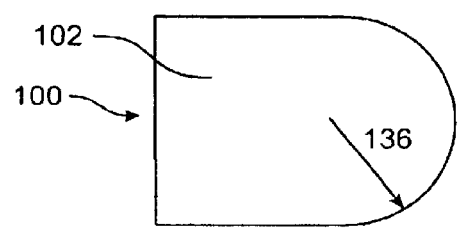
FIG. 5A
FIG. 5B
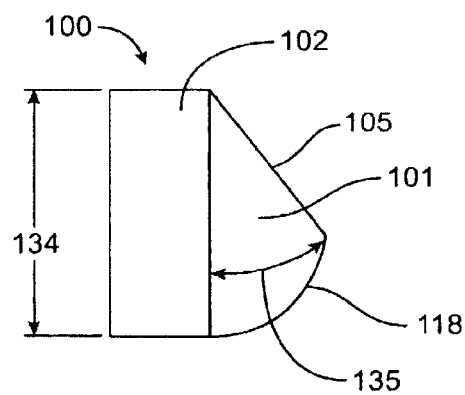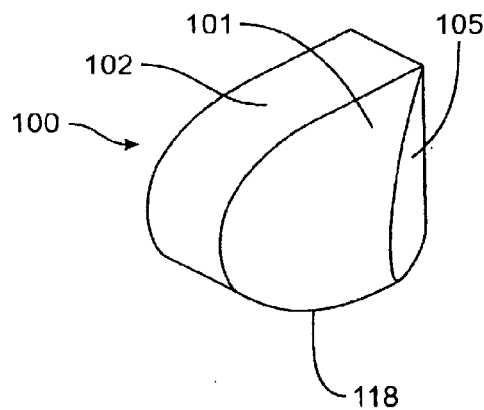
FIG. 5C
FIG. 5D

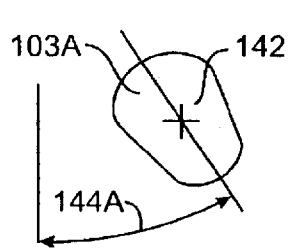 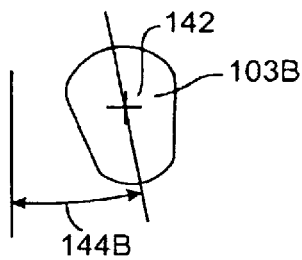 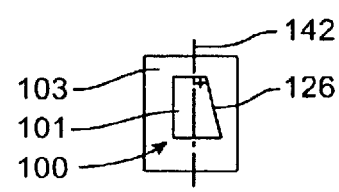
FIG. 6A             FIG. 6B             FIG. 6C
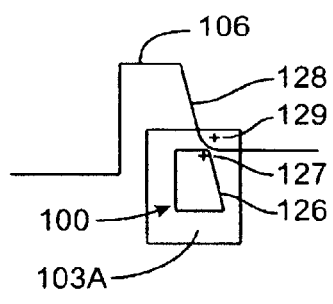 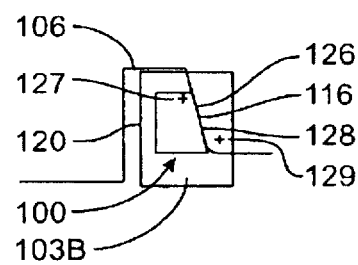
FIG. 6D                    FIG. 6E
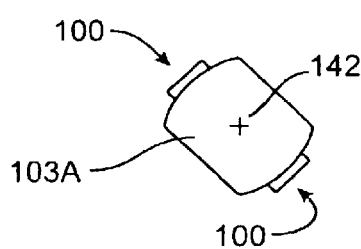 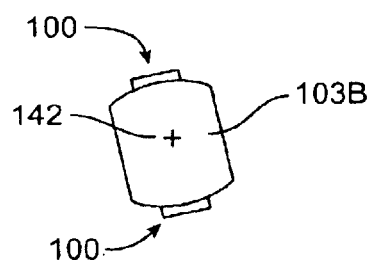
FIG. 6F                    FIG. 6G

SYSTEMS AND METHODS FOR IMPROVED ENGAGEMENT BETWEEN ALIGNERS AND TEETH

BACKGROUND OF THE INVENTION

The present invention is related generally to the field of orthodontics. More particularly, the present invention is related to improved systems and methods for removably attaching a dental positioning appliance to the dental features of a patient during orthodontic treatment.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. The brackets and bands are bonded to the patient's teeth using a suitable material, such as dental adhesive. Once the adhesive has set, the archwire is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontist's office. Moreover, from a patient's perspective, they are unsightly and uncomfortable. Moreover, the archwire and ligatures which connect the brackets in a continuous network make brushing, flossing between the teeth and other dental hygiene procedures difficult, possibly contributing to the development of gingivitis. Consequently, alternative orthodontic treatments are needed. In particular, it would be desirable to use appliances which can be removed by the patient during daily dental hygiene routines, while participating in athletic activities, or for cosmetic purposes.

A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations to a final desired configuration. A full description of an exemplary elastic polymeric positioning appliance is described in U.S. Pat. No. 5,975,893, and in published PCT Publication No. WO 98/58596 which designates the United States and which is assigned to the assignee of the present invention. Both documents are incorporated by reference for all purposes.

In addition to their ease of use, polymeric positioning appliances are generally transparent, providing an improved cosmetic appearance, and impart substantial force on the teeth, due to stiffness of the appliance. The stiffness of an elastic positioning appliance is a result of the modulus of the thermoformable polymer materials from which it is made. The higher the modulus of the materials, the higher the stiffness of the appliance. When a patient positions such an appliance over a prescribed group of teeth, one or more of the teeth will provide a base or attachment region for holding the positioning appliance in place while the stiffness of the polymeric material will impart a resilient repositioning force against one or a portion of the remaining teeth. By designing the appliance to cover the teeth, a much larger contact surface area is afforded compared to traditional spring retainers and wire-based appliances. However, such attaching and repositioning abilities of removable elastic positioning appliances are still dependent on the physical features and configuration of the patient's teeth, palette, and previous dental work, to name a few. For example, shell-like elastic polymeric positioning appliances have difficulty applying certain forces to individual teeth, such as extrusive force (e.g. pulling or raising a tooth relative to the jaw).

Attachment devices anchored to one or several teeth can improve repositioning of the teeth with polymeric appliances. Particularly difficult tooth movements are rotations and extrusions. Using appliances with attachment devices can improve tooth rotation and extrusion. However, during treatment, coupling between an appliance and attachment may become disengaged. This disengagement may occur if a tooth does not move as planned, or moves in a planned direction but not as rapidly as planned. If the planned position of the tooth and attachment differs from the actual position of the tooth and attachment, the receptacle for the attachment formed in the polymeric shell may not properly receive the attachment on the tooth. If the receptacle formed in the polymeric shell does not properly receive the attachment, the force applied to the tooth decreases and the treatment outcome may be less than ideal.

Thus, it would be desirable to provide tooth positioners, systems, and methods which apply adequate force in desired directions to selected teeth at specific times during treatment. In particular, it would be desirable to enable the fabrication and use of removable positioners and systems which can apply extrusive, rotational, and other directional forces which have heretofore been difficult to apply with removable positioners. It would also be desirable to reduce the cost of the orthodontic treatment and retain the patient benefits of a removable appliance in cases where they might not otherwise be available. At least some of these objectives will be met by the designs and methods of the present invention described hereinafter.

SUMMARY OF THE INVENTION

The present invention provides improved methods and systems for using removable polymeric shell appliances for moving teeth. In particular, the present invention configures and positions a force receiving component on a tooth attachment, typically an anchor bonded to a tooth, and a force applying component on the shell appliance, typically a receptacle formed in a wall of the shell which receives the attachment when the shell is placed over the teeth. The attachment and receptacle will be configured to create an engagement point or region therebetween, where the engagement point or region moves or "shifts" as the teeth are repositioned so that the force transmitted is optimized to promote efficient tooth movement throughout the treatment stage using each particular appliance. In one example, both the force applying and the force receiving surfaces are inclined planes which slide over each other as the tooth is moved so that a desired force is maintained on the tooth. In another example, the further receiving and applying surfaces comprise pawl-and-ratchet structures that permit relative positional adjustment as the tooth is moved. Other examples are described hereinafter.

In a first aspect the invention comprises a method of repositioning teeth. The method comprises bonding an attachment having at least one force receiving component to a preselected position on at least one of the teeth. A provided shell repositioning appliance has at least one force transmitting component for transmitting a force. The polymeric shell repositioning appliance is placeable over the teeth so that the force transmitting component and the force receiving component engage each other at a contact point. The contact point is within a locus of engagement, and a position of the contact point adjusts within the locus of engagement as the tooth is repositioned.

In specific embodiments, the locus of engagement extends over a pre-selected distance. The force receiving component and the force transmitting component are positioned so that the force transmitted to at least one tooth which lags its intended position is increased. The polymeric shell appliance placed over the teeth may include a cavity shaped so that a space between the appliance and the tooth permits the tooth to move into an intended position. The polymeric shell and attachment may be shaped to permit the attachment to move relative to the appliance along a channel as the contact point adjusts position within the locus of engagement. In some embodiments a first pair comprises the force transmitting component and a second pair comprises force receiving component, and each member of each pair are positioned on opposing sides of the tooth.

In many embodiments the pre-selected distance over which the locus of engagement extends is at least about 0.5 mm. The distance may be at least about 1 mm. The force transmitting component and force receiving component may be arranged to rotate at least one of the teeth with the transmitted force. In some embodiments the force transmitting component and force receiving component are arranged to extrude at least one of the teeth with the transmitted force. Alternatively, the force transmitting component and force receiving component may be arranged to intrude at least one of the teeth with the force. The force transmitting component and the force-receiving component may comprise a cam and a follower. In some embodiments the contact point adjusts position within the locus of engagement, and this adjustment establishes an equilibrium as the force transmitted to the at least one tooth which lags its intended position is increased.

The force transmitting and force receiving components may be arranged to counter a force from a first surface with a force from a second surface. In specific embodiments the force from the first surface is an intrusive force and the force from the second surface is an extrusive force. Alternatively, the force from the first surface is an extrusive force and the force from the second surface is an intrusive force. A single attachment device may include a first surface and a second surface that counters a force from the first surface. Alternatively, a first attachment device may comprise the first surface and a second attachment device may comprise the second surface. In specific embodiments, the force transmitting component and the force-receiving component comprise a pawl and a ratchet. The force-transmitting component may comprise the ratchet and the force-receiving component may comprise the pawl. Alternatively, the force-transmitting component may include the pawl and the force-receiving component may include the ratchet. In specific embodiments the force receiving component and the force-transmitting component comprise meshing teeth.

In another aspect the invention comprises a system for repositioning teeth in a patient jaw comprising an attachment for bonding to a tooth at a pre-selected position. The attachment has at least one force receiving component for receiving a force. The system also includes a polymeric shell repositioning appliance placeable over at least some of the teeth in the patient jaw. The appliance has at least one force transmitting component positioned to engage the force receiving component of the attachment when the attachment and the force receiving component engage each other at a contact point. The contact point adjusts a contact position within the locus of engagement as the tooth is repositioned.

In some embodiments the locus of engagement extends over a preselected distance. The force receiving component and the force transmitting component are positioned so that the force transmitted to at least one tooth which lags its intended position is increased. In some embodiments the polymeric shell appliance placed over the teeth includes a cavity shaped so that a space between the appliance and the tooth permits the tooth to move into an intended position. The polymeric shell and attachment are shaped to permit the attachment to move relative to the appliance along a channel as the contact point adjusts position within the locus of engagement. A pair may comprise the force transmitting component and the force receiving component, each member of each pair may be on opposing sides of the tooth.

In many embodiments the pre-selected distance over which the locus of engagement extends is at least about 0.5 mm. The distance may be at least about 1 mm. The force transmitting component and the force receiving component maybe arranged to rotate at least one of the teeth with the force. Alternatively, the force transmitting component and the force receiving component may be arranged to intrude at least one of the teeth with the force. The force transmitting component and the force receiving component may be arranged to extrude at least one of the teeth with the force. The contact point may adjust position within the locus of engagement to establish an equilibrium as the force transmitted to the at least one tooth which lags its intended position is increased.

In some embodiments the force transmitting and force receiving components are arranged to counter a force from a first surface with a force from a second surface. In specific embodiments, the force from the first surface is an intrusive force and the force from the second surface is an extrusive force. Alternatively, the force from the first surface is an extrusive force and the force from the second surface is an intrusive force. A single attachment device may comprise the first surface and the second surface. Alternatively, a first attachment device may comprise the first surface and a second attachment device comprises the second surface.

In further embodiments the force transmitting component and the force-receiving component comprise a pawl and a ratchet. In specific embodiments the force-transmitting component comprises the ratchet and the force-receiving component comprises the pawl. Alternatively, the force-transmitting component comprises the pawl and the force-receiving component comprises the ratchet. In an embodiment, the force receiving component and the force-transmitting component comprise meshing teeth.

In yet another aspect the invention comprises a method for designing a polymeric shell tooth repositioning appliance. The method includes locating an attachment on at least one tooth among several teeth of a model to define at least one force receiving component for receiving a transmitted force. The method also includes positioning an attachment receptacle to define at least one force transmitting component in a polymeric shell placeable over the teeth. The force transmitting and force receiving components are shaped to engage each other at a contact point within a locus of engagement. A position of the contact point adjusts within the locus of engagement as the tooth is repositioned.

In specific embodiments the locus of engagement extends over a preselected distance. The force receiving component and the force transmitting component are positioned so that the force transmitted to at least one tooth which lags its intended position is increased. The polymeric shell appliance placed over the teeth may include a cavity shaped so that a space between the appliance and the tooth permits the tooth to move into an intended position. The polymeric shell and attachment are shaped to permit the attachment to move relative to the appliance along a channel as the contact point adjusts its position within the locus of engagement. A prominence may be placed at the locus of engagement to increase the transmitted force.

In some embodiments the model is a computer model and the attachment is a virtual attachment. Modifying the virtual attachment forms a modified virtual attachment. The modified virtual attachment may be for forming the attachment receptacle in the polymeric shell. The modifying of the virtual attachment may include modifying a position of the virtual attachment. The modified virtual attachment may be similar to a shape of at least a portion of the virtual attachment, for example a similar shape formed by truncating a portion of the virtual attachment. In preferred embodiments, the modifying of the virtual attachment increases the force transmitted by the polymeric shell. The modifying of the virtual attachment may include enhancing a surface detail of the virtual attachment to form a modified virtual attachment having enhanced surface detail.

BRIEF DESCRIPTION OF THE DRAWINGS

FIGS. 5A–D illustrate views of an exemplary attachment device for bonding to a tooth for intruding or extruding the tooth.

FIGS. 6A–G illustrate a method of rotating a tooth in accord with an aspect of the present invention.

DETAILED DESCRIPTION OF THE INVENTION

Figure 1A:
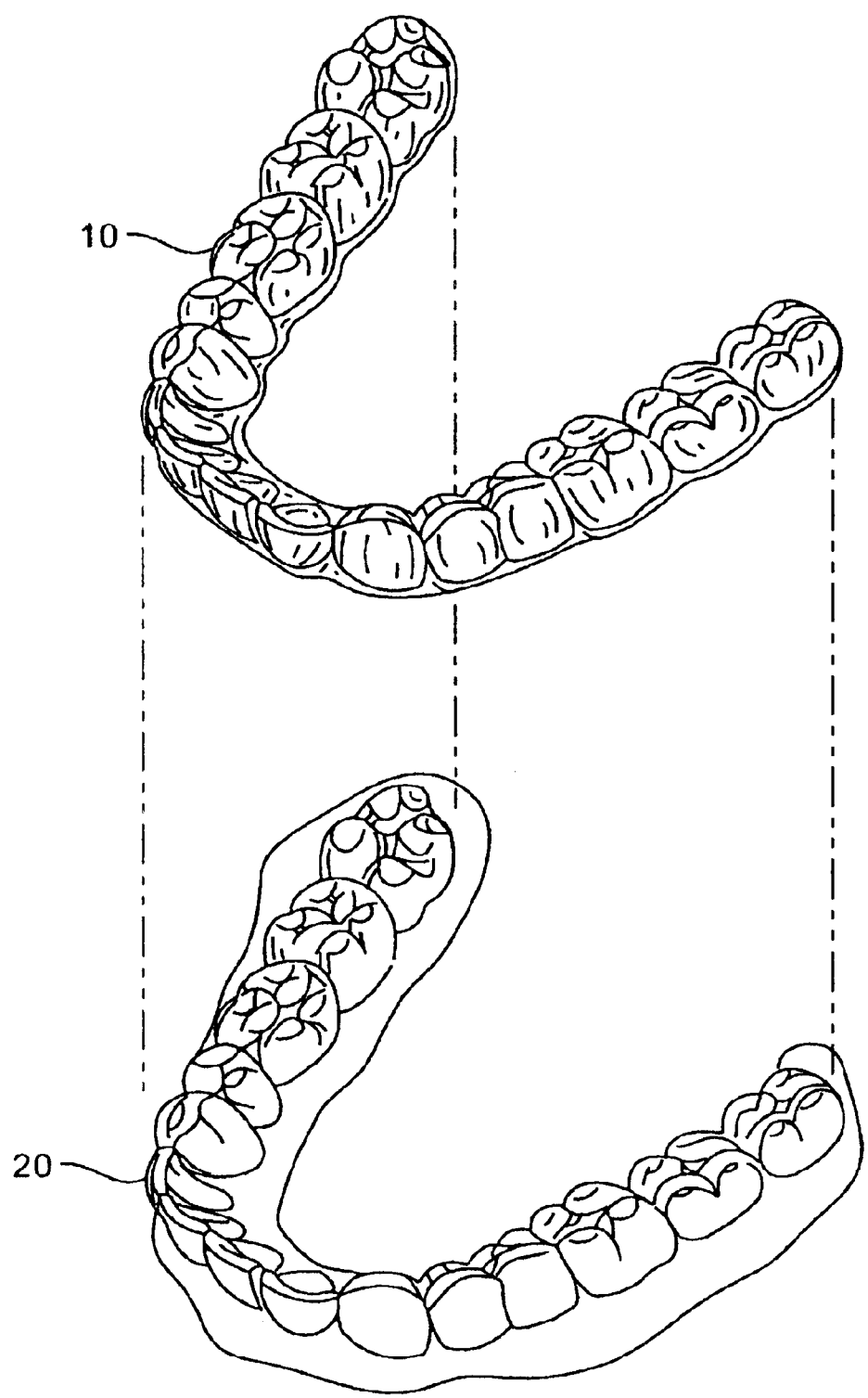
FIG. 1A illustrates an appliance for incorporating the present invention positioned above a set of teeth.

The present invention provides improved systems and methods for moving teeth by positioning appliances over teeth. Appliances are often referred to as aligners. An appliance 10 and a set of teeth 20 are illustrated in FIG. 1A. Specific systems and methods for producing the appliances are described in U.S. Pat. No. 5,975,893, the full disclosure of which is incorporated herein by reference. The teeth are bonded to attachment devices to effect rotation, translation, intrusion and extrusion of the teeth. Attachment devices and appliances for incorporating the present invention are described in U.S. Pat. No. 6,309,215, the full disclosure of which is incorporated herein by reference. A series of appliances are positioned over the teeth and attachments to reposition teeth from an initial position to a final position. Interactions of the attachment devices and appliances include cam and follower, meshing gear, and ratchet and pawl type interactions. The interactions of the present invention deliver force to a tooth over a range of motion, thereby providing an improved engagement between the appliance and tooth. This engagement is maintained if a tooth lags an intended position during treatment.

Each appliance is designed to incrementally move each treated tooth to an intended position. When an appliance is first positioned over the teeth, a treated tooth typically is not located at the intended position prescribed by the geometry of the appliance. In other words, the treated tooth position lags the intended position. For example, if a previous appliance has treated a tooth and the position of the treated tooth has moved to the intended position prescribed by the previous appliance, the treated tooth position will lag the intended position prescribed by a new appliance. The intended position will lag the actual position by the incremental motion intended between the previous and new appliances. If prior appliances have intended motion of a tooth, the tooth may not have achieved an intended position from a previous appliance. In this case the position of the tooth will lag the intended position of the current appliance by more than the intended incremental motion between appliances. Incremental motion of an intended position of a treated tooth between sequential appliances is typically between about 0.1 and 1.0 mm, preferably between about 0.2 and 0.6 mm and more preferably between about 0.25 and 0.5 mm.

The present invention has the advantage of engaging a lagging tooth by employing a movable locus of engagement. The movable locus of engagement typically has a range of engagement permitting engagement between the appliance and attachment even if the treated tooth position lags the intended tooth position by a distance greater than the intended incremental motion of the tooth between sequential appliances. A space in the appliance is provided for the tooth to move into an intended position, and a channel in the appliance permits the attachment to move along the locus of engagement as described in more detail herein below. As used herein, a locus of engagement having a substantial range of motion encompasses a locus of engagement having a range of motion greater than a distance of an intended incremental motion of a tooth treated by an appliance. A range of movement of a locus of engagement is typically between about 0.1 and 4.0 mm, preferably between about 0.2 and 2 mm, and more preferably between about 0.5 and 1.5 mm.

A patient's teeth are repositioned from an initial tooth arrangement to a final tooth arrangement by placing a series of incremental position adjustment appliances in the patient's mouth. Conveniently, the appliances are not affixed and the patient may place and replace the appliances at any time during the procedure. The first appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the patient's mouth, where the final appliance has a geometry selected to progressively reposition teeth from the last intermediate arrangement to the final tooth arrangement.

The polymeric appliance 10 of FIG. 1A is preferably formed from a thin sheet of a suitable elastomeric polymeric, such as Tru-Tain 0.03 in. thermal forming dental material, Tru-Tain Plastics, Rochester, Minn. 55902. Usually, no wires or other means will be provided for holding the appliance in place over the teeth. In accord with an aspect of the present invention, it will be desirable or necessary to provide individual attachments on teeth with corresponding receptacles in the appliance 10 so that the appliance can apply a force on the tooth which would generally not be possible in the absence of such an attachment.

The methods incorporating the present invention will generally rely on manipulating an initial digital data set (IDDS) at a computer or workstation having a suitable graphical user interface (GUI) and software appropriate for viewing and modifying the images. The IDDS is obtained from digitized measurements of the teeth. While some embodiments incorporating the present invention will rely on computer manipulation of digital data, the systems of the present invention comprising multiple dental appliances having incrementally differing geometries may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described in the patent literature, using pressure and vacuum molding techniques. While such manual creation of the appliance systems of the present invention will generally be much less preferred, systems so produced will come within the scope of the present invention.

Figure 1B:
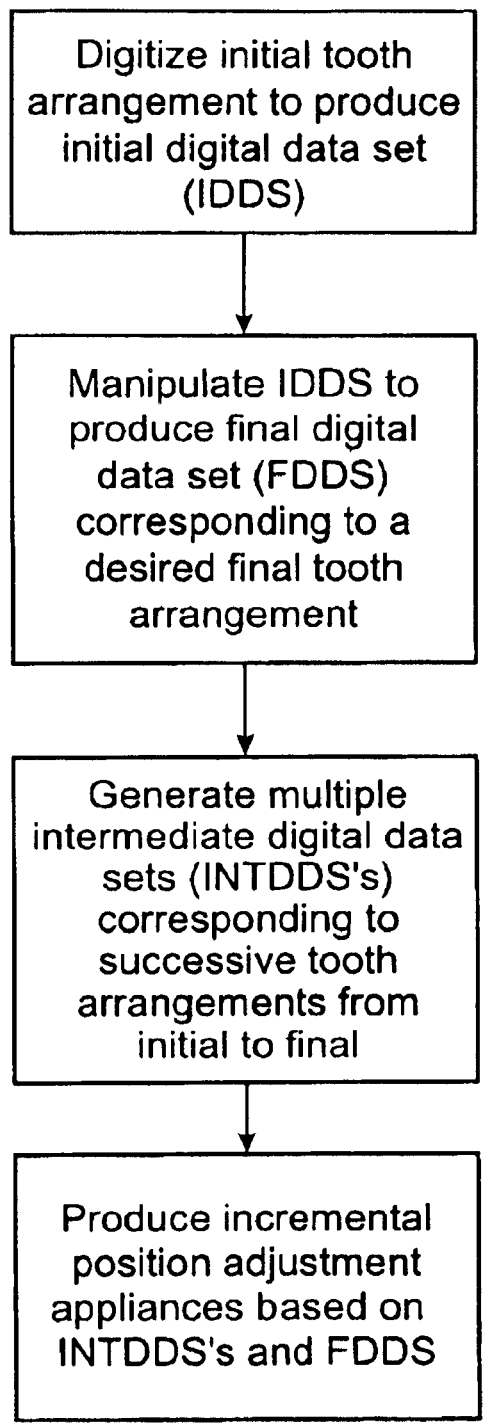
FIG. 1B illustrates a method of generating digital data sets for incorporating the present invention.

Referring to FIG. 1B, after the IDDS has been obtained, the digital information will be introduced to the computer or other workstation for manipulation. In one approach, individual teeth and other components will be "cut" to permit their individual repositioning or removal from the digital data. After thus "freeing" the components, the user will often follow a prescription or other written specification provided by the treating professional. Alternatively, the user may reposition them based on the visual appearance or using rules and algorithms programmed into the computer. Once the user is satisfied with the final arrangement, the final tooth arrangement is incorporated into a final digital data set (FDDS).

Based on both the IDDS and the FDDS, a plurality of intermediate digital data sets (INTDDS's) are generated to correspond to successive intermediate tooth arrangements. The system of incremental position adjustment appliances can then be fabricated based on the INTDDS's.

Figure 1C:
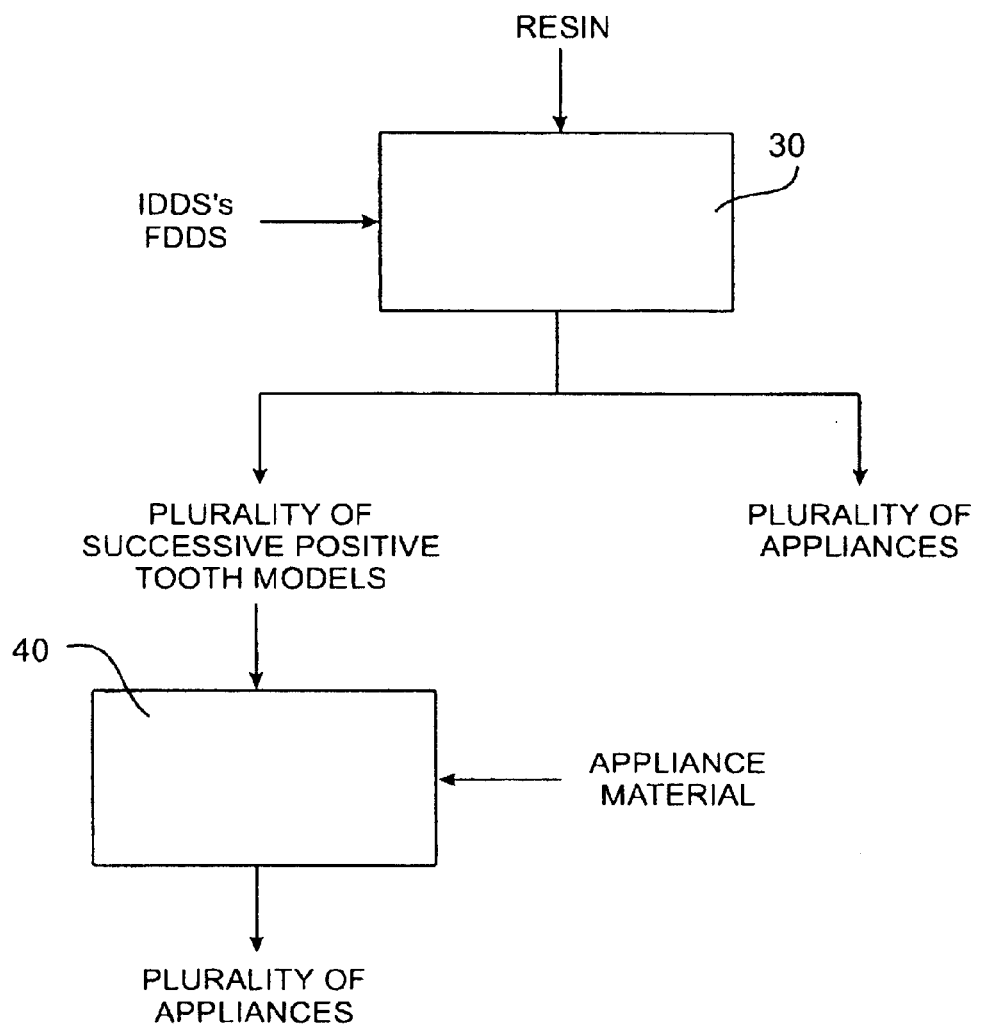
FIG. 1C illustrates alternative processes for producing a plurality of appliances utilizing digital data sets incorporating the present invention and representing the intermediate and final appliance designs.

Once the intermediate and final data sets have been created, the appliances may be fabricated as illustrated in FIG. 1C. Preferably, fabrication methods will employ a rapid prototyping device 30 such as a stereolithography machine. A particularly suitable rapid prototyping machine is Model SLA-250/50 available from 3D SYSTEM, Valencia, Calif. The rapid prototyping machine 30 will selectively harden a liquid or other non-hardened resin into a three-dimensional structure which can be separated from the remaining non-hardened resin, washed, and used either directly as the appliance or indirectly as a mold for producing the appliance. The prototyping machine 30 will receive the individual digital data sets and produce one structure corresponding to each of the desired appliances. Generally, because the rapid prototyping machine 30 may utilize a resin having non-optimum mechanical properties and which may not be generally acceptable for patient use, it will be preferred to use the prototyping machine to produce molds which are, in effect, positive tooth models of each successive stage of the treatment. After the positive models are prepared, a conventional pressure or vacuum molding machine may be used to produce the appliances from a more suitable material, such as 0.03 inch thermal forming dental material, available from TRU-TAIN PLASTICS, Rochester, Minn. 55902. Suitable pressure molding equipment is available under BIOSTAR™ from GREAT LAKES ORTHODONTICS, LTD., Tonawanda, N.Y. 14150. The molding machine 40 produces each of the appliances directly from the positive tooth model and the desired material. Suitable vacuum molding machines are available from RAINTREE ESSIX, INC.

Figure 1D:
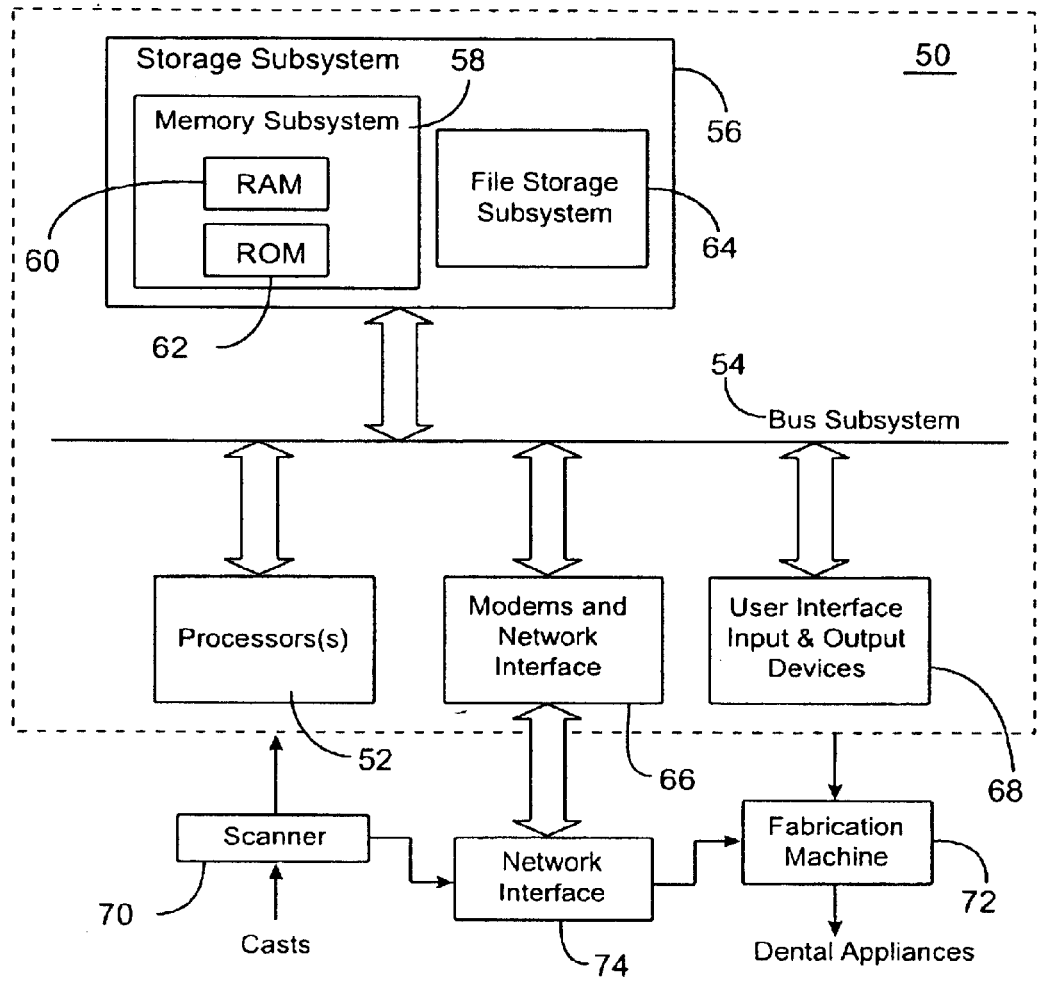
FIG. 1D illustrates a computer system for incorporating an aspect of the present invention.

A simplified block diagram of a data processing system 50 is illustrated in FIG. 1D. Data processing system 50 typically includes at least one processor 52 which communicates with a number of peripheral devices over bus subsystem 54. These peripheral devices typically include a storage subsystem 56 (memory subsystem 58 and file storage subsystem 64), a set of user interface input and output devices 68, and an interface to outside networks 66, including the public switched telephone network. This interface is shown schematically as "Modems and Network Interface" block 66, and is coupled to corresponding interface devices in other data processing systems over communication network interface 74. Data processing system 50 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 56 maintains the basic programming and data constructs that provide the functionality of the present invention. The software modules discussed above are typically stored in storage subsystem 56. Storage subsystem 56 typically comprises memory subsystem 58 and file storage subsystem 64.

Memory subsystem 58 typically includes a number of memories including a main random access memory (RAM) 60 for storage of instructions and data during program execution and a read only memory (ROM) 62 in which fixed instructions are stored. In the case of Macintosh-compatible personal computers the ROM would include portions of the operating system; in the case of IBM-compatible personal computers, this would include the BIOS (basic input/output system).

File storage subsystem 64 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by SYQUEST and others, and flexible disk cartridges, such as those marketed by IOMEGA. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor.

Bus subsystem 54 is shown schematically as a single bus, but a typical system has a number of buses such as a local bus and one or more expansion buses, as well as serial and parallel ports. Network connections are usually established through a device such as a network adapter on one of these expansion buses or a modem on a serial port. The client computer may be a desktop system or a portable system.

Scanner 70 is responsible for scanning casts of the patient's teeth obtained either from the patient or from an orthodontist and providing the scanned digital data set information to data processing system 50 for further processing. In a distributed environment, scanner 70 may be located at a remote location and communicate scanned digital data set information to data processing system 50 over network interface 74.

Fabrication machine 72 fabricates dental appliances based on intermediate and final data set information received from data processing system 50. In a distributed environment, fabrication machine 72 may be located at a remote location and receive data set information from data processing system 50 over network interface 74.

Figure 1E:
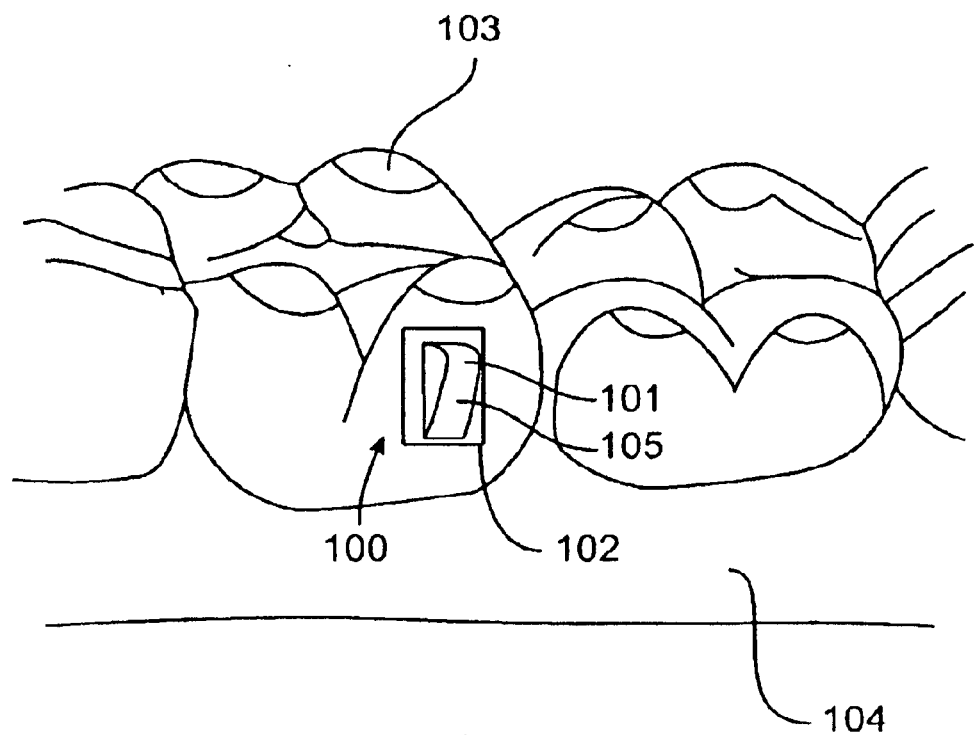
FIG. 1E illustrates a patient's tooth having an attachment device for incorporating the present invention.

Referring to FIG. 1E, an embodiment of an attachment device 100 is shown bonded to a tooth 103 above gingiva 104. The attachment device 100 may be comprised of an attachment body 101 having a base 102, which may be integral or separate and permanently or removable joined. The attachment device 100 includes a surface 105 for engaging an appliance to form a movable locus of engagement. The moveable locus of engagement permits relative motion between the appliance and attachment and transmits force from the appliance to the attachment and tooth over a range of motion.

Figure 2:
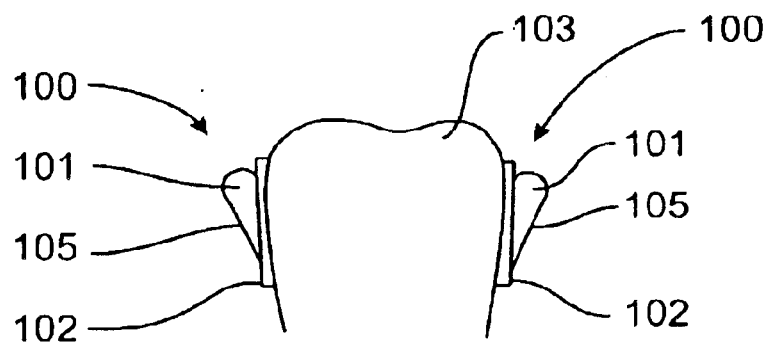
FIG. 2 illustrates a mesial view of a pair of exemplary attachment devices for extruding a tooth in accord with an aspect of the present invention.
Figure 3:
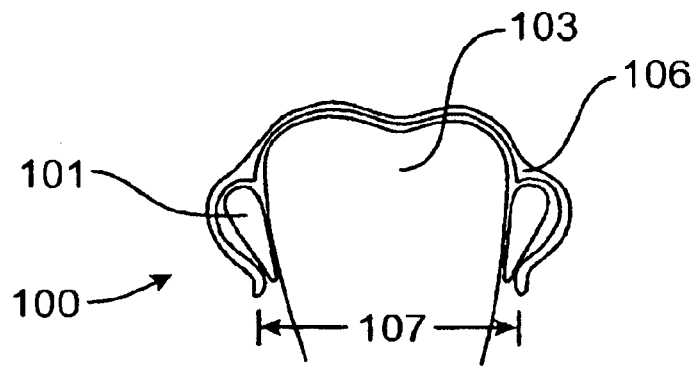
FIG. 3 illustrates a mesial view of a pair of attachment devices as in FIG. 2 covered by an appliance with a tooth in an intended position.
Figure 4:
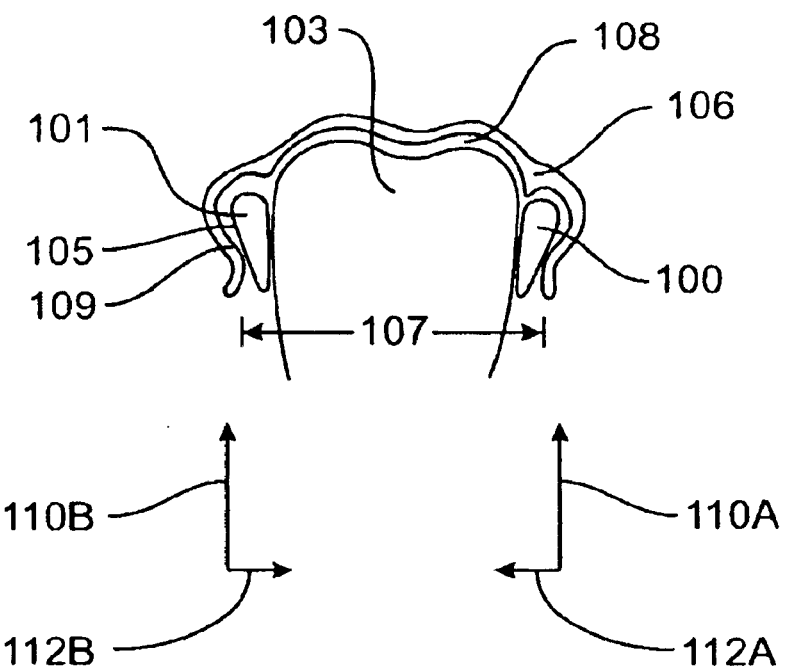
FIG. 4 illustrates a mesial view of appliance engaging a pair of attachment devices in a manner similar to a cam and follower in response to the tooth lagging an intended position.
Figure 4A:
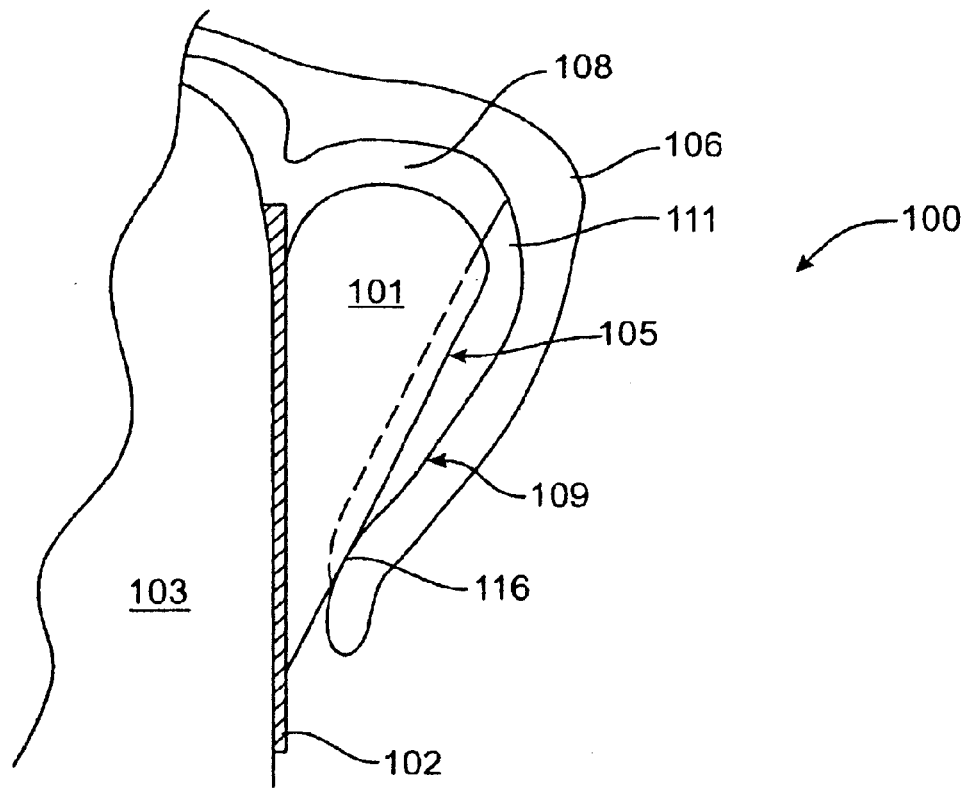
FIG. 4A illustrates an enlarged mesial view of an attachment device covered by an appliance as in FIG. 4.
Figure 4B:
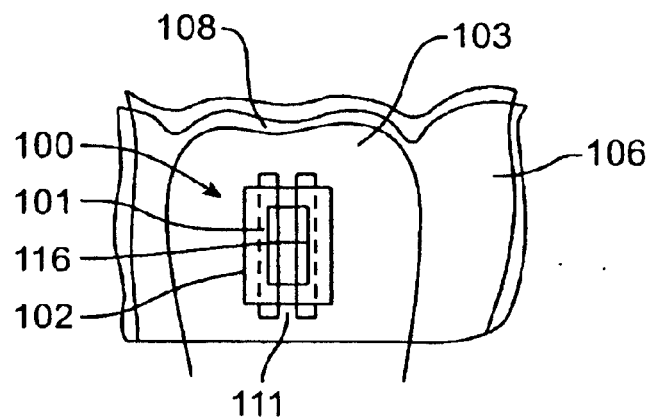
FIG. 4B illustrates a buccal view of an attachment device as in FIG. 4.

A pair of attachment devices 100 illustrated in FIG. 2 is for extruding a tooth 103. An appliance 106 positioned over a tooth 103 and attachments 100 are illustrated in FIG. 3. As illustrated in FIG. 3, the tooth is at an intended position. During treatment of the tooth, a position of the tooth lags an intended position as illustrated in FIGS. 4 and 4A and as described above. A surface 105 of a body 101 of an attachment 100 engages a surface 109 of the appliance 106. The engagement of surface 105 of attachment 100 with surface 109 of appliance 106 forms a movable locus of engagement 116 at a contact point or contact region. As used herein a contact point encompasses a localized region of contact between a surface 109 of an appliance 106 and a surface 105 of an attachment 100. A locus of engagement 116 is maintained during relative motion of tooth 103 to appliance 106. A buccal view of an attachment device as in FIG. 4 is illustrated in FIG. 4B. A channel 111 formed in appliance 106 permits a locus of engagement 116 to be maintained over a substantial range of motion. A space 108 permits tooth 103 to move into an intended position. In an alternate embodiment a channel is formed in a body 101 of attachment 100.

A dimension 107 across the appliance 106 increases, thereby stretching appliance 106 and increasing forces applied to tooth 103 as illustrated by arrows 110A, 110B, 112A and 112B. The opposing positions of the pair of attachment devices 100 cancel the horizontal applied forces 112A and 112B. The resulting extruding force applied to the tooth is the sum of forces 110A and 110B. A space 108 permits the tooth to advance in response to the applied forces 110A and 110B. An increasing prominence of surface 105 as tooth 103 deviates from an intended position increases stretching deformation of appliance 106 across dimension 107. Forces applied to tooth 103 increase in response to tooth 103 deviating from an intended position. This increase in force in response to an increased error in the actual tooth position relative to the intended position provides corrective movement of tooth 103.

An intended position of a treated tooth is prescribed in an appliance geometry for the treated tooth. The attachment body 101 follows a path of motion prescribed by the surface 109 of appliance 106. The surface 109 of appliance 106 is a follower that follows the motion prescribed by the attachment 100 which is a cam. A series of sequential appliances may be used to provide an increase motion of attachment 100 and tooth 103. The appliance positioned over the tooth is a force transmitting component which applies force to the force receiving attachment devices that in turn transfer the received force to the tooth. Increasing deformation of appliance 106 increases the force transmitted from the appliance to the attachment and tooth. As a tooth increasingly lags an intended position, deformation of the appliance and the force transmitted to the tooth via an attachment increase. As described above, the tooth moves in response to the forces applied to the tooth. As the tooth lags an intended position, forces applied to the tooth increase, and as the tooth advances toward and intended position, forces applied to the tooth decrease. Movement ceases when equilibrium is established between the forces applied and transmitted to the tooth and the position achieved by the tooth.

Figure 4C:
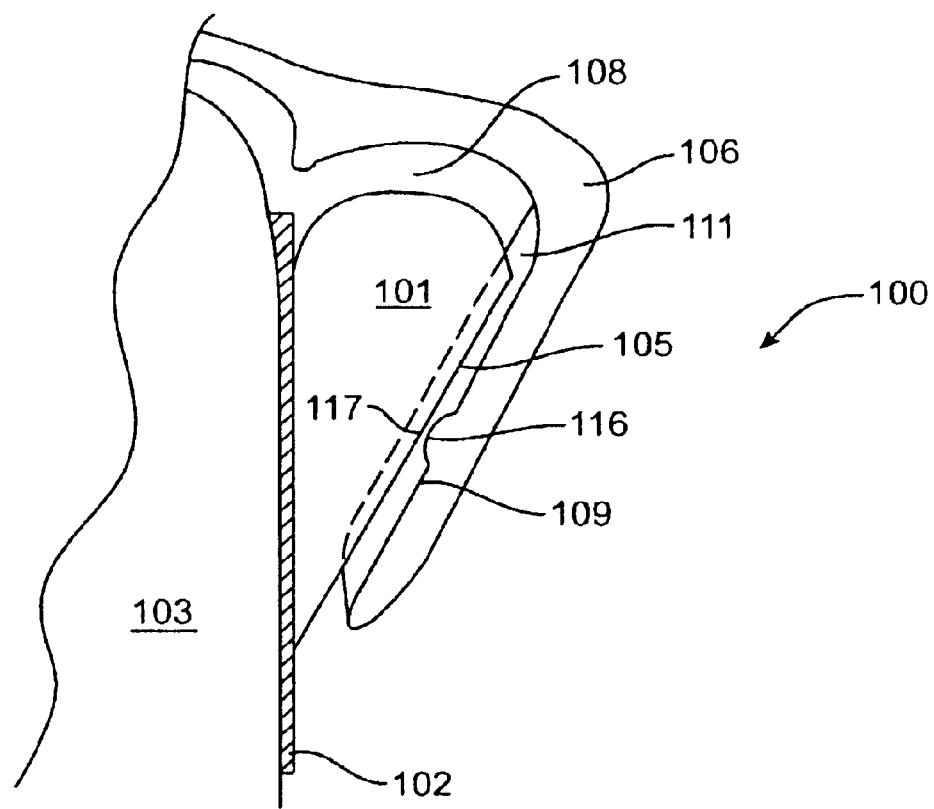
FIG. 4C illustrates a mesial view of an alternate cam and follower embodiment in which the appliance includes a prominence for increasing a force applied to the attachment and tooth.

A mesial view of an alternate cam and follower embodiment is illustrated in FIG. 4C. The appliance includes a prominence 117, or pressure point, at locus of engagement 116 for increasing a force applied to the attachment and tooth.

Figure 5:
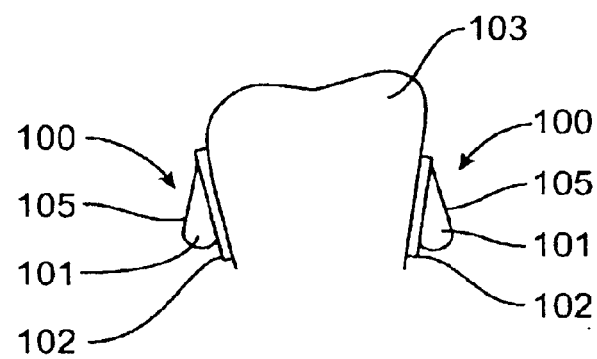
FIG. 5 illustrates a mesial view of a pair of attachment devices bonded to a tooth that are for intruding the tooth.

As illustrated in FIG. 5, an embodiment of the invention uses a pair of wedge shaped attachments 100 for intruding a tooth 103. An appliance has a surface for engaging the attachments to form a moving locus of engagement as described above. The moving locus of engagement exerts an intruding force on the tooth.

Referring to FIGS. 5A–5D, an exemplary embodiment of a wedge shaped attachment 100 has a surface 105 for engaging the appliance, a transition surface 118, and a base 102. Front, side, top and isometric views of the exemplary embodiment are illustrated in FIGS. 5A–5D respectively. Transition surface 118 provides a smooth transition from surface 105 to base 102 and also permits a size of base 102 to increase thereby providing improved bonding to tooth 103. Height 130, length 134 and width 132 of attachment 100 are varied to desirably reposition tooth 103 without interfering with teeth or lingual or labial surfaces of the mouth. Also, the size of base 102 does not exceed a size of exposed tooth for bonding base 102. A length 134 of attachment 100 is typically between 2 and 6 mm and preferably between 3 and 5 mm. A width 132 of attachment 100 is typically between 1 and 4 mm and preferably between 2 and 3 mm. An angle of inclination 135 of surface 105 is also varied to desirably reposition tooth 103. The angle of inclination 135 is typically between 10 and 60 degrees, preferably between 20 and 50 degrees and more preferably between 30 and 40 degrees. A radius of curvature 136 of attachment base 102 may also be varied, and is typically half of the width 132 of attachment device 100. Transition surface 118 varies to provide a smooth transition between base 102 and inclined surface 105.

Referring to FIGS. 6A–6G in which a method of rotating a tooth is illustrated, an initial tooth 103A rotation angle 144A is determined as illustrated in FIG. 6A. An intended rotated tooth 103B rotation angle 144B is determined as illustrated in FIG. 6B. An attachment 100 having a body 101 with an inclined surface 126 is positioned on a tooth 103 relative to an intended axis of rotation 142 as illustrated in FIG. 6C and FIG. 6F. An appliance 106 is positioned near initial tooth 103A as illustrated in FIG. 6D. A portion 129 of surface 128 of appliance 106 is positioned near a portion 127 of surface 126 of attachment 100. The surface 128 of appliance 106 engages and slides along surface 126 of attachment device 100 and forms locus of engagement 116 as illustrated in FIG. 6E. Follower surface 128 of appliance 106 drives the motion of surface 126 on attachment 100 and tooth 103 and drives tooth and attachment toward an equilibrium as described above. The portion 129 of surface 128 of appliance 106 slides over portion 127 of surface 126 of attachment 100. The rotated tooth 103B is driven toward equilibrium between the force transmitted by the surface 128 of appliance 106 and the force received by the surface 126 of attachment 100. A space 120 permits the tooth to move into an intended position and extends a range of motion of locus of engagement 116. The rotated tooth 103B in a final intended position rotated about axis of rotation 142 is illustrated in FIG. 6G. Rotation of tooth from an initial tooth 103A position to a rotated tooth 103B position may be achieved with several appliances 106.

Figure 7:
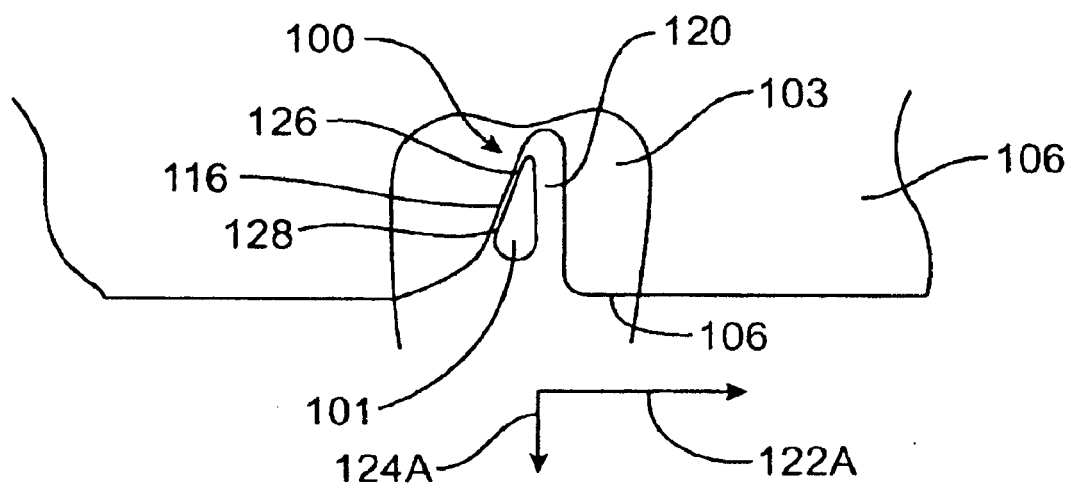
FIG. 7 illustrates a buccal view of an embodiment of the present invention comprising an attachment device and appliance for rotating a tooth in response to occlusal gingival motion of an engaging surface of the appliance.
Figure 7A:
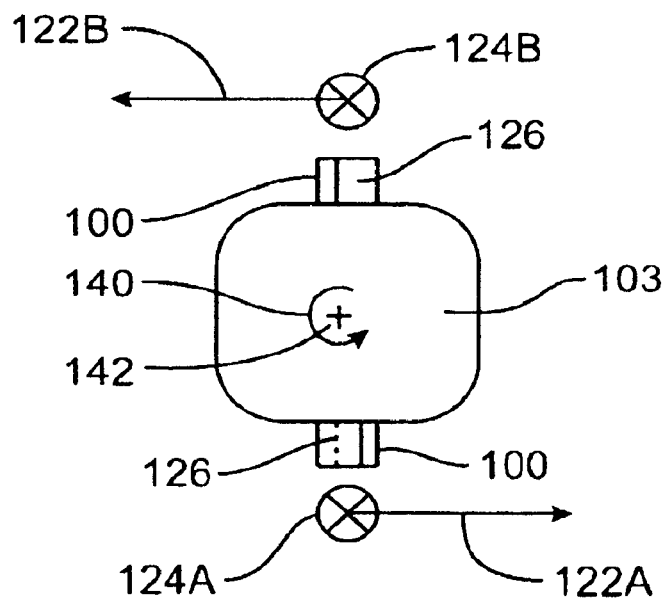
FIG. 7A illustrates an occlusal view of a pair of attachment devices for rotating a tooth as in FIG. 7.

Referring to FIG. 7 an embodiment of an attachment 100 for rotating a tooth 103 by an engaging appliance 106 is illustrated. Rotation of tooth 103 occurs in response to occlusal-gingival motion of a surface 128 of appliance 106. Attachment 100 has a body 101 having a sloped surface 126 that engages a surface 128 of appliance 106. The engagement of a surface 128 of appliance 106 with a surface 126 of attachment 100 forms a moveable locus of engagement 116. A space 120 permits the tooth to move into an intended position and extends a range of motion of locus of engagement 116. The force transmitted from the appliance to the attachment and tooth has a rotational component 122A and an intrusive component 124A. As illustrated in FIG. 7A, a pair of attachments 100 provide forces 122A and 122B that are radially displaced from axis of rotation 142 and form a force couple for rotating 140 tooth 103 about an axis of rotation 142. An angle of inclination of surface 126 encompasses an angle measured with reference to the occlusal-gingival direction, or vertical direction as seen in FIG. 7. An angle of inclination of the surface 126 of attachment 100 is between about 5 and 60 degrees. Preferably an angle of inclination is between about 10 and 40 degrees. More preferably the angle of inclination is between about 15 and 30 degrees.

Figure 8:
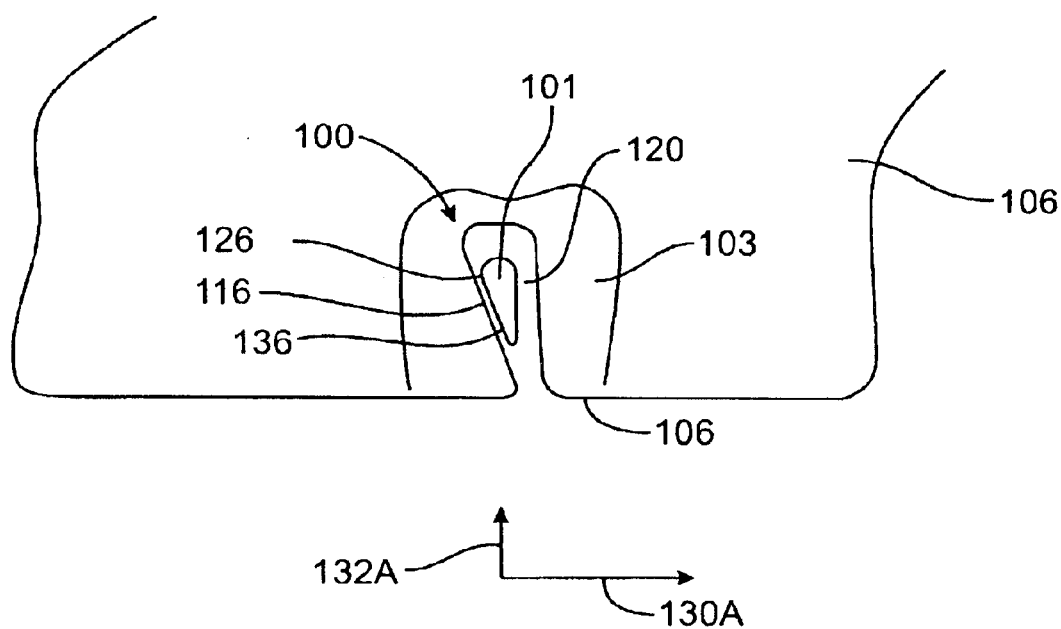
FIG. 8 illustrates a buccal view of an embodiment of the present invention comprising an attachment device and appliance for rotating a tooth in response to gingival occlusal motion of an engaging surface of the appliance.
Figure 8A:
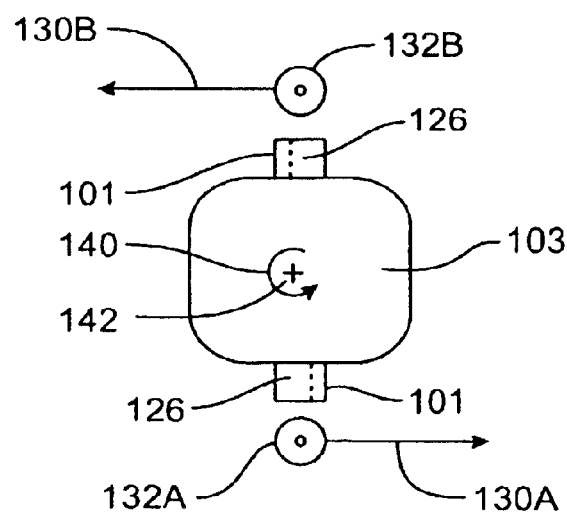
FIG. 8A illustrates an occlusal view of a pair of attachment devices for rotating a tooth as in FIG. 8.

Referring to FIG. 8 an alternate embodiment of an attachment 100 for rotating a tooth 103 by engaging an appliance 106 is illustrated. Rotation of tooth 103 occurs in response to gingival-occlusal motion of a surface 136 of appliance 106. Attachment 100 has a body 101 having a sloped surface 126 that engages a surface 136 of appliance 106. The engagement of a surface 136 of appliance 106 with a surface 126 of attachment 100 forms a moveable locus of engagement 116. A space 120 permits the tooth to move into an intended position and extends a range of motion of locus of engagement 116. The force transmitted from the appliance to the attachment has a rotational component 130A and extrusive force component 132A. As illustrated in FIG. 8A, a pair of attachments 100 provide forces 130A and 130B that form a force couple for rotating 140 tooth 103 about an axis of rotation 142.

Figure 9:
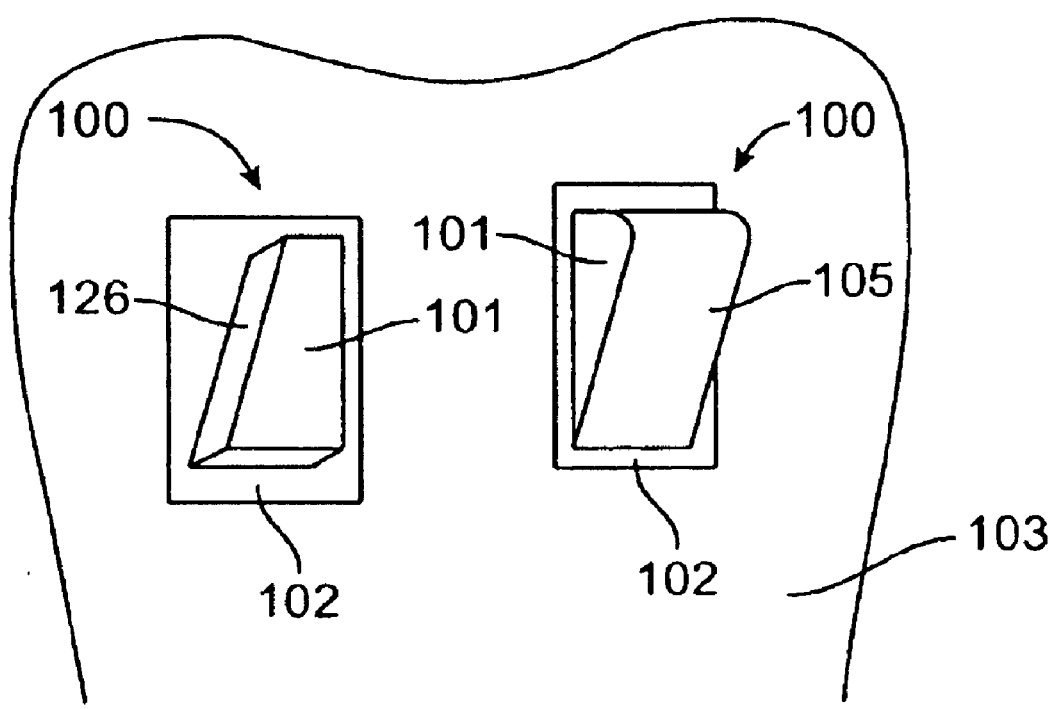
FIG. 9 illustrates a buccal view of an embodiment of the present invention comprising a pair of attachment devices for rotating the tooth by generating a rotational force from a first attachment that also generates a slight intrusive force, and a second attachment for countering the intrusive force with an extrusive force from a surface of the second attachment.

Referring to FIG. 9 illustrating a buccal view of a pair of attachment devices bonded to a side of a tooth 103, attachments 100 include surfaces 105 and 126. Surface 126 rotates tooth 103 and produces a slight intrusive force as described above. Surface 105 produces an extrusive force on tooth 103 as described above. The extrusive force of surface 105 counters the slight intrusive force of surface 126 while surface 126 rotates tooth 103.

Figure 10:
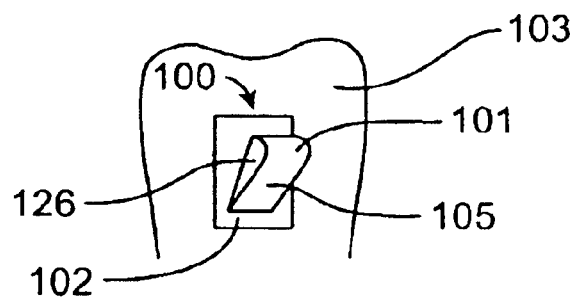
FIG. 10 illustrates a buccal view of an installed attachment device having a surface for rotating the tooth and a surface for extruding the tooth to counter an intrusive force of the surface for rotating the tooth.
Figure 10A:
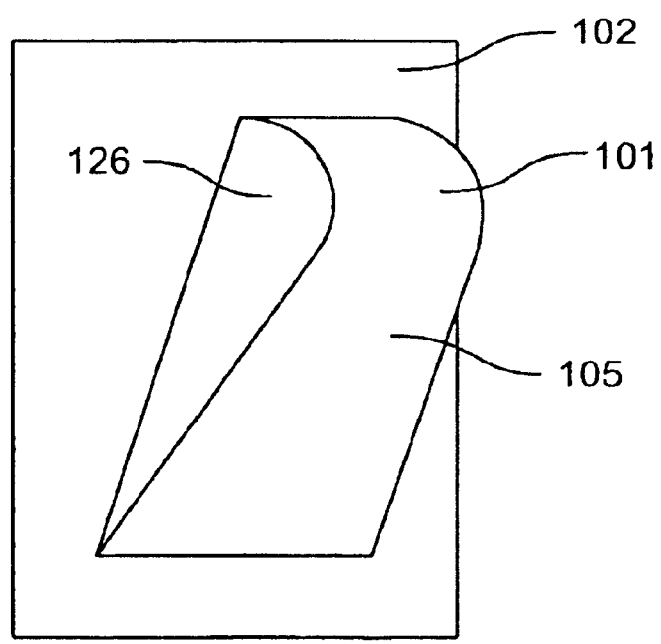
FIG. 10A illustrates an enlarged view of an attachment device as in FIG. 10.
Figure 11A:
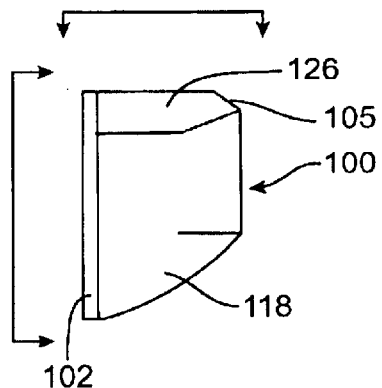
FIGS. 11A–D illustrate views of an exemplary attachment device for rotating a tooth that has a surface for rotating the tooth, a surface for extruding the tooth in response to a slight intrusion force from the surface for rotating, and a smooth transition surface for gently tapering the slopes of surfaces.
Figure 11B:
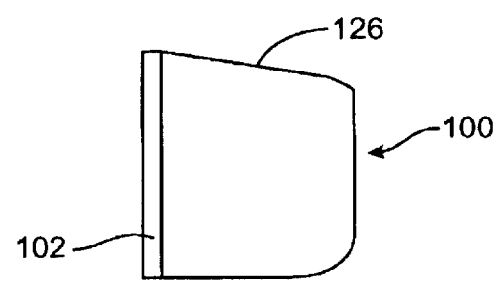
Figure 11C:
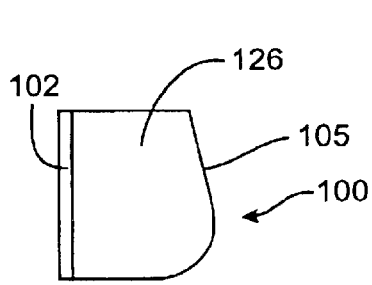
Figure 11D:
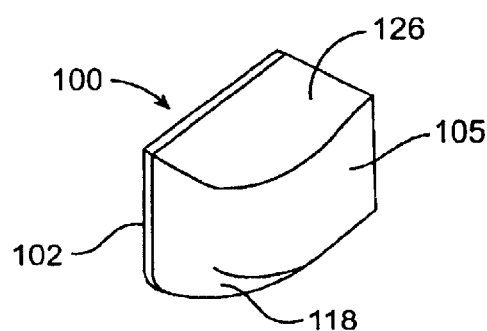

A buccal view of an installed attachment device is illustrated in FIG. 10. A surface 126 for rotating a tooth 103 and a surface 105 for extruding a tooth are combined as a single attachment 100. An enlarged view of an attachment device as in FIG. 10 is illustrated in FIG. 10A.

An exemplary attachment device 100 for rotating a tooth is illustrated in FIGS. 11A–D. A surface 126 for rotating a tooth and a surface 105 for extruding a tooth are combined as a single attachment device 100. Attachment device 100 also includes a transition surface 118. Transition surface 118 provides a gentle transition between surfaces 105 and 126 and base 102. Transition surface 118 permits base 102 to be enlarged while providing a smooth transition between surfaces 105 and 126. In practice it may be desirable to increase a size of base 102 to increase an area of bonding between base 102 and an exposed surface of a tooth.

Figure 12A:
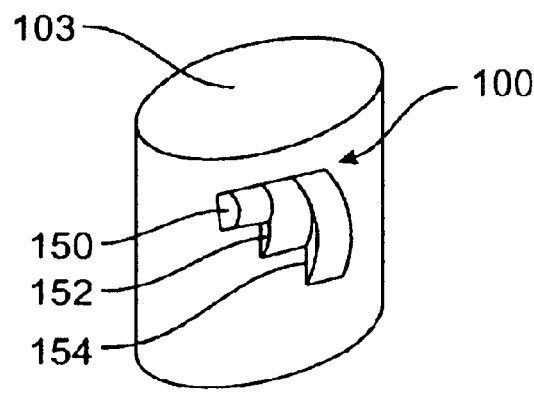
FIG. 12A illustrates several abutting attachment devices mounted to a tooth for altering force directions over time.

Several abutting attachment devices 100 mounted to a tooth 103 are illustrated in FIG. 12A. Individual attachment devices 150, 152 and 154 provide an alteration of force directions over time. An appliance engages an appropriate attachment device for transmitting a desired force to a tooth.

Figure 12B:
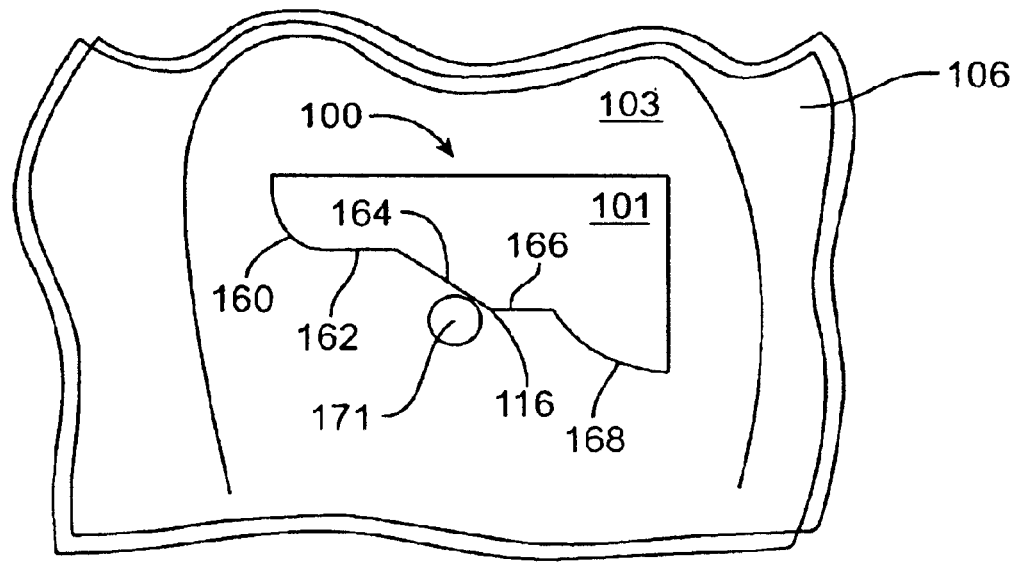
FIG. 12B illustrates an attachment device mounted to a tooth and providing several surfaces to engage a surface of the appliance.

An alternate embodiment of an attachment device 100 mounted to a tooth 103 and providing several surfaces 160, 162, 164, 166 and 168 to engage a surface of an appliance is illustrated in FIG. 12B. The attachment 100 includes curved surfaces 160 and 168, flat surfaces 162 and 166 and sloped surface 164. An appliance 106 controls motion of an attachment 100 that follows a path of motion prescribed by a sequence of sequential appliances 106. The appliance 106 includes a follower 171. The follower 171 engages a surface 164 of attachment 100 to form a locus of engagement 116. During the course of treatment, the follower 171 and locus of engagement 116 move along surfaces 160, 162, 164, 166 and 168 with subsequent appliances. The moving locus of engagement 116 extrudes tooth 103. In alternate embodiments tooth 103 is intruded by the force transmitted by the appliance at the moving locus of engagement. In a further embodiment, the attachment includes a single round surface and the appliance includes several surfaces for engaging the attachment.

Figure 12C:
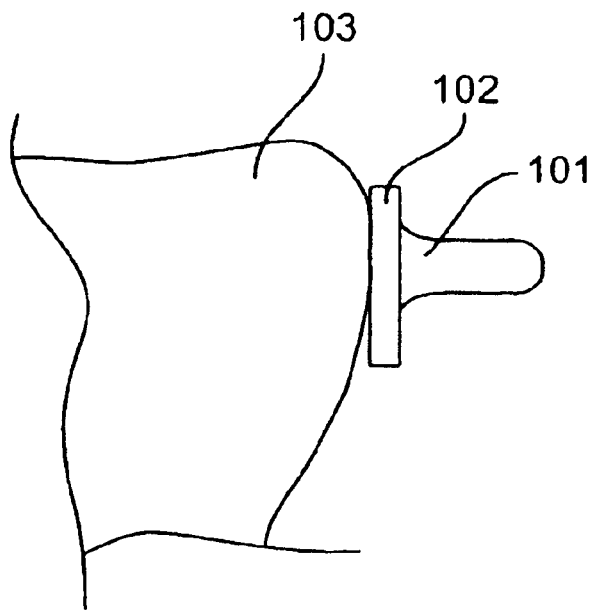
FIGS. 12C and 12D illustrate an attachment device for following a surface of an appliance.
Figure 12D:
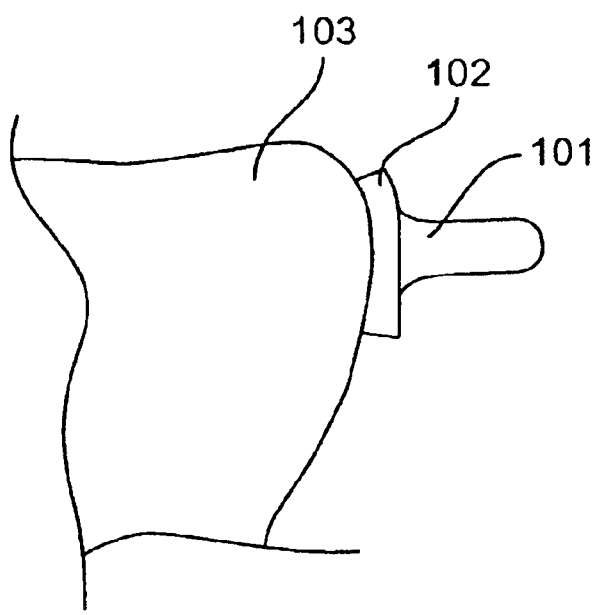

Attachment devices using a body 101 having a singe round surface to engage an appliance are illustrated in FIGS. 12C and D. A base 102 of an attachment is flat as illustrated in FIG. 12C and curved to match a tooth 103 as illustrated in FIG. 12D.

Figure 12E:
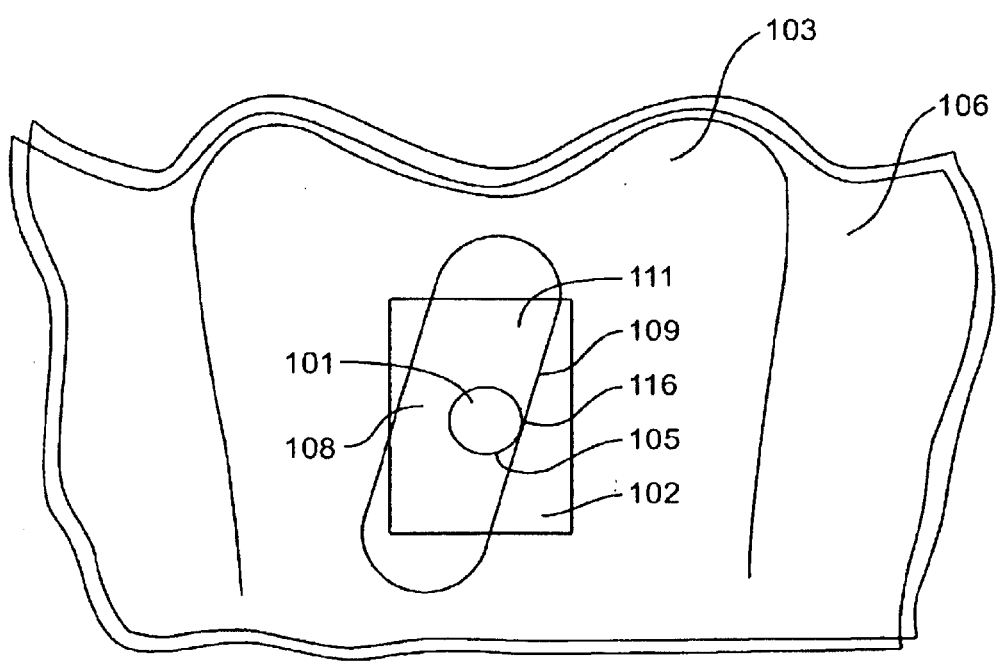
FIG. 12E illustrates an appliance for rotating a tooth and an attachment as in either of FIGS. 12C and 12D.

A round attachment device as described above is used to rotate a tooth in an embodiment of the present invention illustrated in FIG. 12E. Engaging a surface 109 of an appliance 106 with a surface 105 of an attachment body 101 forms a locus of engagement 116. A pair of attachments and an appliance are used to rotate the tooth 103 as described above.

Figure 13A:
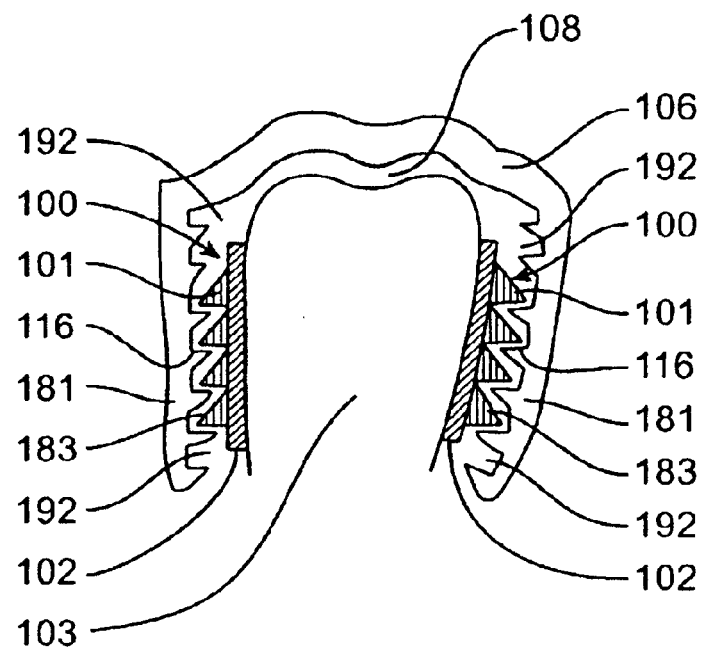
FIGS. 13A–13B illustrate an attachment device and appliance for extruding a tooth in accord with an aspect of the present invention in which engagement between an appliance and attachment are as meshing gears.
Figure 13B:
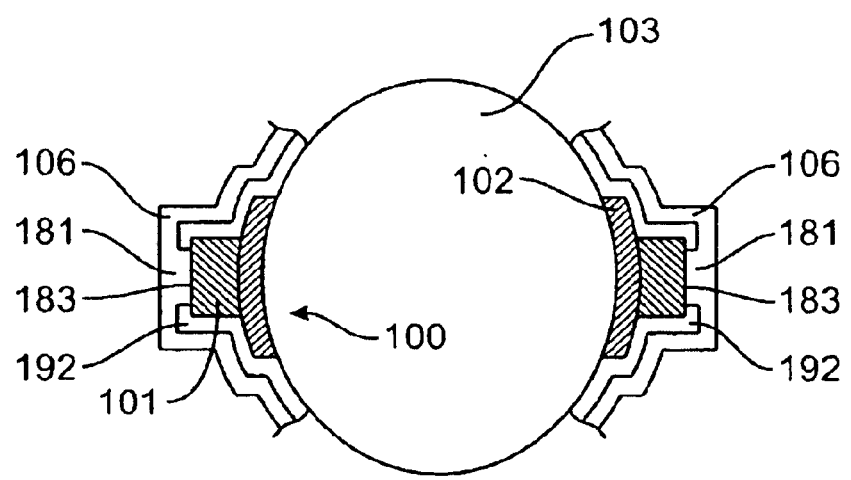

A further embodiment of an attachment device and appliance forming a moving locus of engagement 116 as meshing gears is illustrated with a buccal view in FIG. 13A and an occlusal view in FIG. 13B. A pair of attachment devices 100 is mounted to tooth 103 to extrude tooth 103. An appliance 106 is positioned over tooth 103. Each attachment device 100 includes several teeth 183 for meshing with several teeth 181 of appliance 106. A channel 192 permits relative motion of tooth 103 to appliance 106 over a range of motion and maintains locus of engagement 116 as tooth 103 moves relative to appliance 106 over a substantial range of motion. A space 108 permits tooth 103 to extrude into an intended position.

Figure 14A:
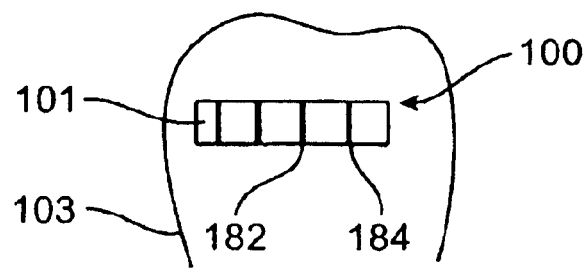
FIGS. 14A–14D illustrate an attachment device and an appliance for rotating a tooth in accord with an embodiment of the present invention in which an appliance as a pawl engages an attachment engaging as a ratchet.
Figure 14B:
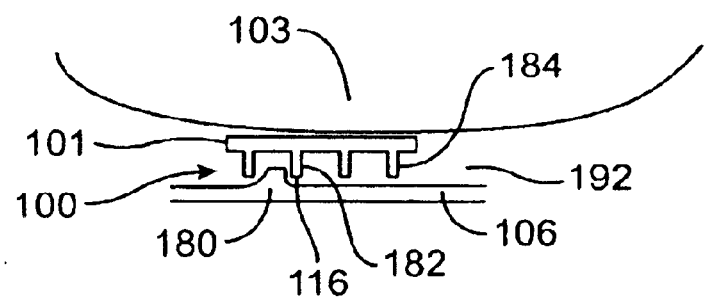
Figure 14C:
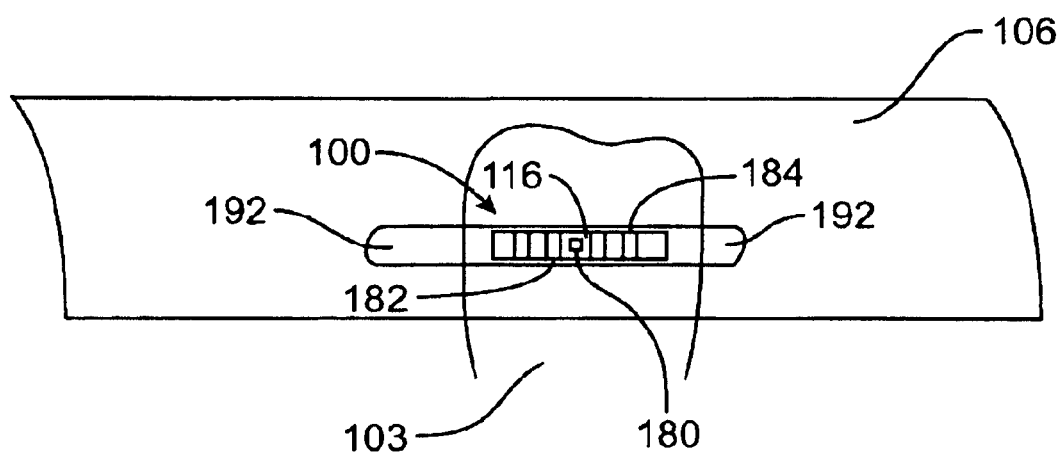
Figure 14D:
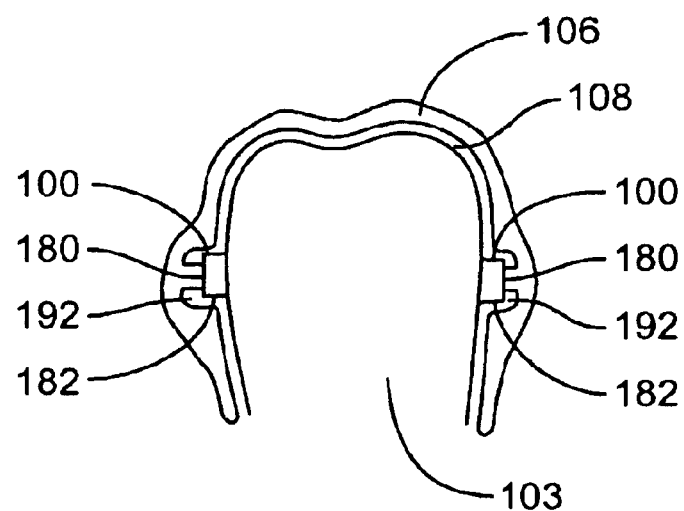

A further embodiment for rotating teeth is illustrated in FIGS. 14A–D. A buccal view of FIG. 14A illustrates a tooth 103 with a bonded attachment 100. Attachment 100 includes a ratchet 182 with several teeth 184. An occlusal view is illustrated in FIG. 14B. Appliance 106 includes a pawl 180 for engaging teeth 184 of ratchet 182. A movable locus of engagement 116 forms as pawl 180 of appliance 106 engages teeth 184 of ratchet 182 of attachment 100. A channel 192 permits relative motion of tooth 103 to appliance 106 over a substantial range of motion. Several teeth 184 of ratchet 182 and channel 192 maintain locus of engagement 116 over a substantial range of motion. A buccal view is illustrated in FIG. 14C and a mesial view in FIG. 14D. Channel 192 formed in appliance 106 extends for several mm beyond teeth 184 of ratchet 182. Pawl 180 engages teeth 184 of ratchet 182 to form movable locus of engagement 116. Locus of engagement 116 is maintained over several mm of motion.

Figure 15:
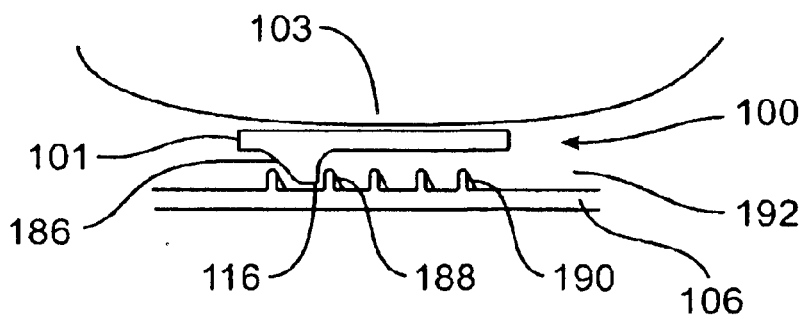
FIG. 15 illustrates an attachment device and an appliance for rotating a tooth in accord with an aspect of the present invention in which an appliance as a ratchet engages an attachment engaging as a pawl.

Another embodiment for rotating teeth with a pawl and ratchet is illustrated in FIG. 15. Attachment 100 includes a pawl 186 formed in attachment body 101. Appliance 106 includes a ratchet 188 comprising several teeth 190 for engaging pawl 186 over a substantial range of motion. A channel 192 formed in appliance 106 permits engagement locus 116 to be maintained over several mm of relative motion of tooth 103 to appliance 106.

Figure 16:
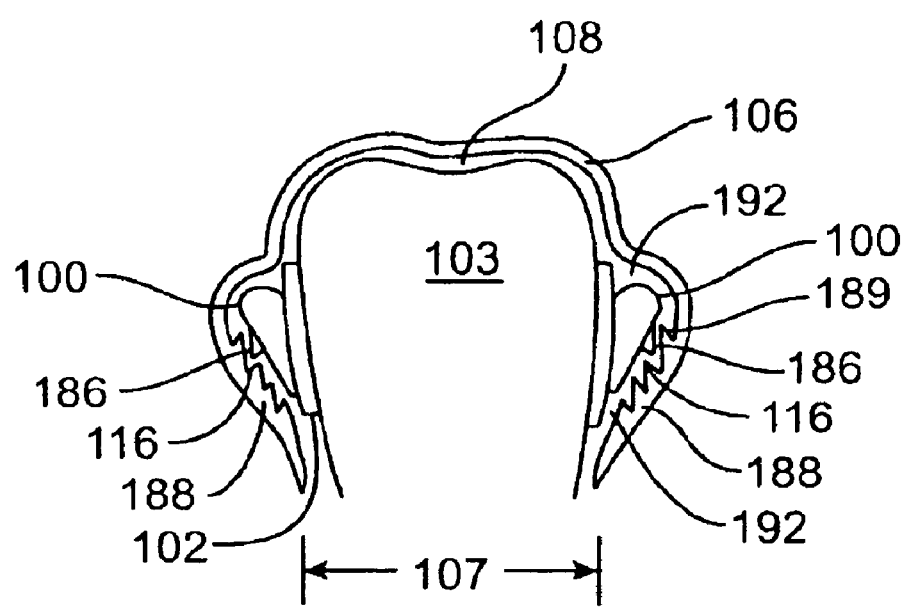
FIG. 16 illustrates a pair of attachment devices as pawls and an appliance as ratchets for extruding a tooth in accord with an aspect of the present invention in which a force of engagement between the pawl and ratchet increases in response to the tooth lagging an intended position during treatment.

A further embodiment illustrated in FIG. 16 includes a pawl 186 of attachment 100 mounted to increasingly engage the teeth 189 of a ratchet 188 of an appliance 106. A space 108 permits a tooth 103 to move into an intended position resulting in extrusion of tooth 103. A channel 192 permits tooth 103 to move relative to appliance 106 over a substantial range of motion. Locus of engagement 116 is maintained over several mm of motion of tooth 103 relative to appliance 106 by several teeth 189 of ratchet 188 and channel 192. Tooth 103 lagging an intended position relative to appliance 106 increases a dimension across 107 appliance 106. This increased dimension deforms and stretches appliance 106 and increases engagement between teeth 189 of ratchet 188 of appliance 106 and pawl 186 of attachment 100. A force of engagement between the force receiving pawl 186 and force transmitting ratchet increases in response to the tooth lagging an intended position during treatment. Motion ceases when an equilibrium is established as described above.

Figure 17A:
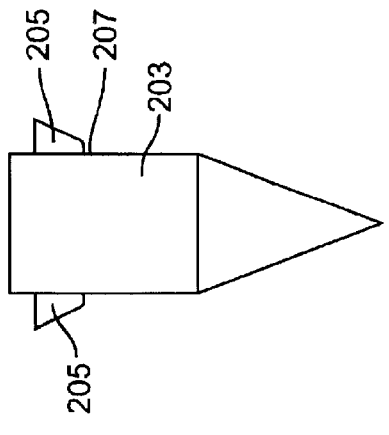
FIGS. 17A–E illustrate a process for forming appliances to engage attachments with increased a force.
Figure 17B:
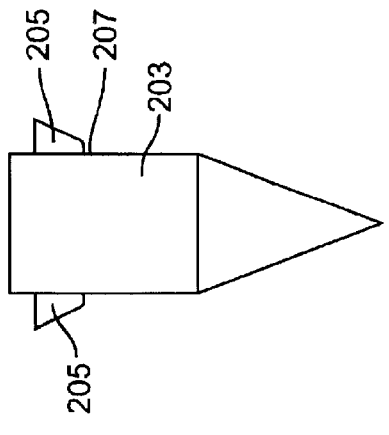
Figure 17C:
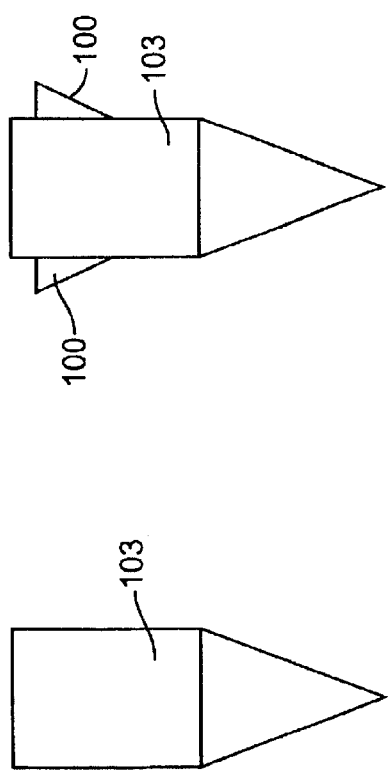
Figure 17D:
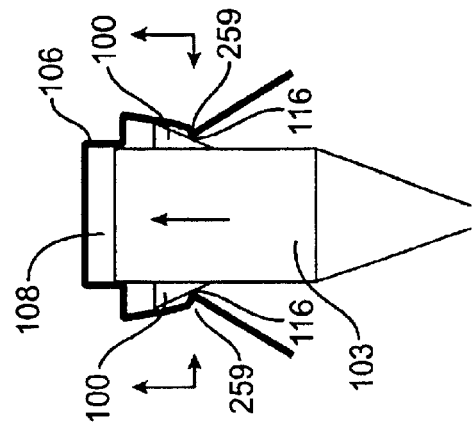
Figure 17E:
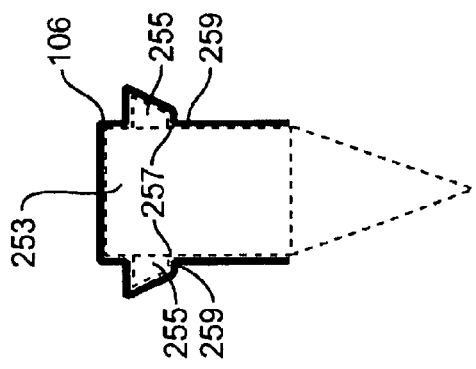

A process for making appliances with increased force transmission to an attachment is illustrated in FIGS. 17A–17E. A tooth 103 has a pair of bonded attachments 100 as illustrated in FIG. 17B. A virtual tooth 203 is made on a computer from a digital data set representing tooth 103 as illustrated in FIG. 17C. Virtual tooth 203 is bonded to virtual attachment 205. Virtual attachment 205 is a representation of attachment 100. Virtual attachment 100 is modified to produce decreased surface relief over a portion of attachment 205. For example, a notch 207 is formed on the end of the virtual attachment. In alternate embodiments, notch 207 is positioned elsewhere on attachment 100. Notch 207 is also described as a virtual pressure point as the appliance formed over this point will produce increased force on an attachment. Virtual attachment 205 may be enlarged to form a channel and enable a locus of engagement to move over a substantial range. A positive tooth mold 253 and a positive attachment mold 255 are made from virtual tooth 203 and virtual attachment 205 as illustrated in FIG. 17D. Positive attachment mold 255 also includes notch 257 and may include shapes for creating a channel for extending a range of motion of a moving locus of engagement. An appliance 106 is formed to fit over positive molds of tooth 253, attachment 255 and notch 257. The form fit attachment 106 includes increased prominence 259 fitting into notch 257. Appliance 106 is positioned over a tooth 103 and attachments 100 and produces locus of engagement 116 as illustrated in FIG. 17E. Locus of engagement 116 is formed at increased prominence 259 of appliance 106. Increased prominence 259 increases stretching of appliance 106 and increases force transmitted from appliance 106 and force received by attachment device 100. Increased prominence 259 is also described as a pressure point.

Figure 18:
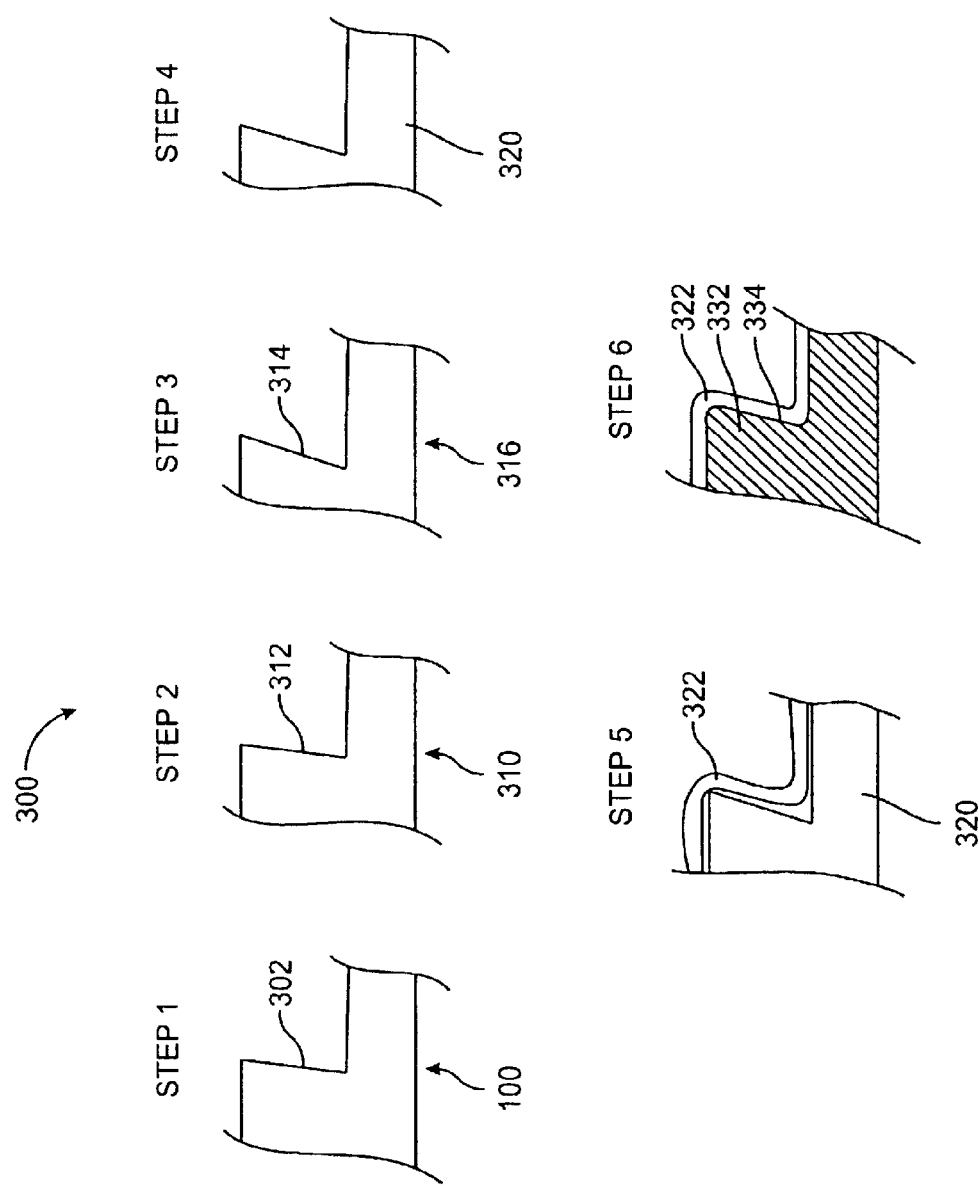
FIG. 18 illustrates an improved process for forming an appliance to fit fine detail of an attachment device.

An improved process 300 for making an attachment 100 having a surface formed to a desired shape is illustrated in FIG. 18. During the formation of an appliance receptacle, the appliance polymer may bridge across corners and other sharp transitions of the mold. This effect is referred to as webbing and is at least partially corrected as illustrated in FIG. 18. A desired shape formed in surface 302 of an attachment 100 is illustrated at STEP 1. A virtual attachment 310 having the desired shape formed in virtual surface 312 is illustrated at STEP 2. Virtual attachment 310 and shaped virtual surface 312 have dimensions matching attachment 100 and desired surface 302. At STEP 3 virtual surface 312 is modified to form modified virtual surface 314 of modified virtual attachment 316. Modified virtual surface 314 has a modified bevel to correct for webbing. A positive mold 320 is formed from modified virtual attachment 316 as illustrated in STEP 4. An appliance 322 is formed from positive mold 320 as illustrated in STEP 5. At STEP 6 an attachment 332 having a surface 334 closely matching desired surface 302 is formed from appliance 322.

Figure 19A:
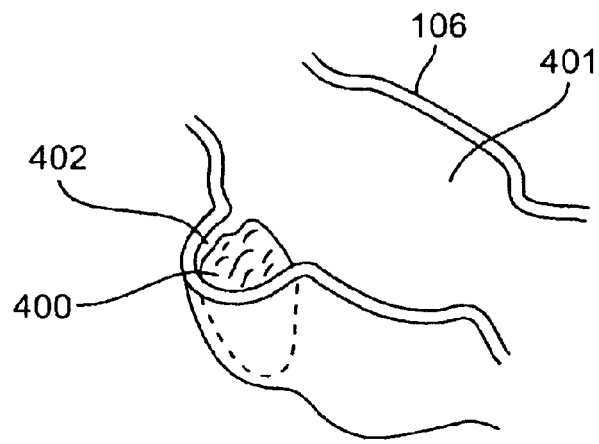
FIGS. 19A–C illustrate a process for forming an attachment in situ on a patient.
Figure 19B:
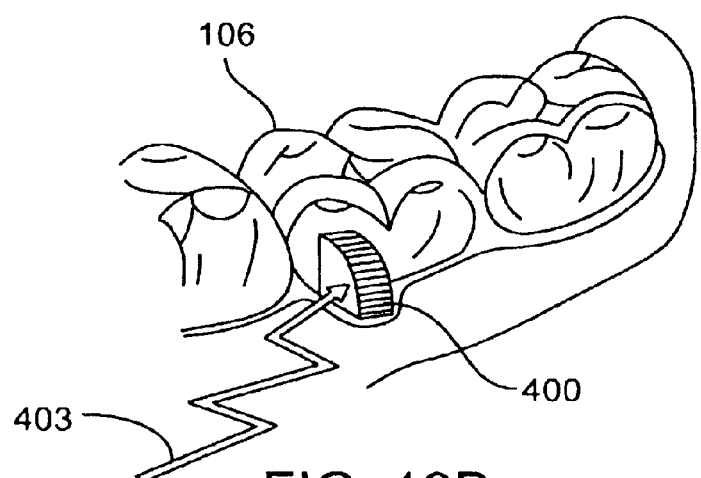
Figure 19C:
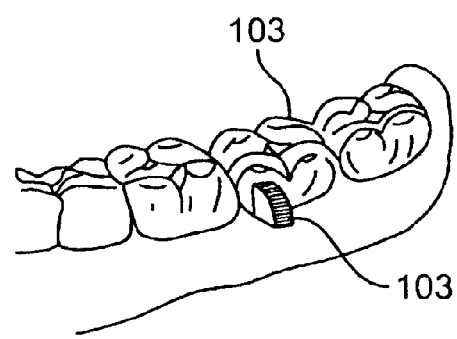

In a preferred embodiment, the attachment is formed in situ on the patient with a polymerizing material. The method of casting with a polymerizing material is similar to the method of basic casting described in U.S. Pat. No. 6,309,215, the full disclosure of which is incorporated herein by reference. In one embodiment, an elastic positioning appliance 106 is formed over a mold 320 of an attachment device 100, as previously depicted in FIG. 18. At this point, a malleable polymerizing material 400 may be placed into the negative impression 402 in an appliance 106. FIG. 19A illustrates an enlarged view of the underside of a portion of the appliance 106, revealing a receiving cavity 401 for a tooth 103 and the negative impression 402 of an attachment device 100 filled with a polymerizing material 400. The appliance 106 is seated in position in the oral cavity, as shown in FIG. 19B. The polymerizing material 400 is in contact with the desired dental surface, in this case a tooth 103, and is positioned in the proper location. The material 400 is polymerized (depicted by jagged arrow 403) by any means, such as an external stimulus. Upon removal of the appliance 106, the formed attachment device 100 remains in place on the tooth 103, as shown in FIG. 19C. Although a specific attachment is shown in FIG. 19C, any suitable attachment as described above can be formed.

Additional details of the attachment forming process are described in U.S. Pat. No. 6,309,215 and in U.S. patent application Ser. No. 10/040,269 filed Oct. 29, 2001, and issued as U.S. Pat. No. 6,705,863, the full disclosures of which are incorporated herein by reference.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of repositioning teeth, the method comprising:
   bonding an attachment having at least one force receiving component to a preselected position on at least one of the teeth; and
   providing a polymeric shell repositioning appliance, wherein the polymeric shell has at least one force transmitting component for transmitting a force;
   wherein the polymeric shell repositioning appliance is placeable over the teeth so that the force transmitting component and the force receiving component engage each other at a contact point within a locus of engagement, wherein a position of the contact point adjusts within the locus of engagement as the tooth is repositioned.

2. The method of claim 1 wherein the locus of engagement extends over a pre-selected distance.

3. The method of claim 2 wherein the force receiving component and the force transmitting component are positioned so that the force transmitted to at least one tooth which lags its intended position is increased.

4. The method of claim 2 wherein the polymeric shell appliance placed over the teeth includes a cavity shaped so that a space between the appliance and the tooth permits the tooth to move into an intended position.

5. The method of claim 4 wherein the polymeric shell and attachment are shaped to permit the attachment to move relative to the appliance along a channel as the contact point position adjusts within the locus of engagement.

6. The method of claim 1 wherein a first pair comprises the force transmitting component and a second pair comprises force receiving component, each member of each pair being positioned on opposing sides of the tooth.

7. The method of claim 2 wherein the distance is at least about 0.5 mm.

8. The method of claim 7 wherein the distance is at least about 1 mm.

9. The method of claim 1 wherein the force transmitting component and force receiving component are arranged to rotate at least one of the teeth with the force.

10. The method of claim 1 wherein the force transmitting component and force receiving component are arranged to extrude at least one of the teeth with the force.

11. The method of claim 1 wherein the force transmitting component and force receiving component are arranged to intrude at least one of the teeth with the force.

12. The method of claim 1 wherein the force transmitting component and the force receiving component comprise a cam and a follower.

13. The method of claim 3 wherein the position of the contact point adjusts within the locus of engagement as the force transmitted to the at least one tooth which lags its intended position is increased to establish an equilibrium.

14. The method of claim 3 wherein the force transmitting and force receiving components are arranged to counter a force from a first surface with a force from a second surface.

15. The method of claim 14 wherein the force from the first surface is an intrusive force and the force from the second surface is an extrusive force.

16. The method of claim 14 wherein the force from the first surface is an extrusive force and the force from the second surface is an intrusive force.

17. The method of claim 14 wherein a single attachment device comprises the first surface and the second surface.

18. The method of claim 14 wherein a first attachment device comprises the first surface and a second attachment device comprises the second surface.

19. The method of claim 5 wherein the force transmitting component and the force receiving component comprise a pawl and a ratchet.

20. The method of claim 19 wherein the force transmitting component comprises the ratchet and the force receiving component comprises the pawl.

21. The method of claim 19 wherein the force transmitting component comprises the pawl and the force receiving component comprises the ratchet.

22. The method of claim 5 wherein the force receiving component and the force transmitting component comprise meshing teeth.

23. A system for repositioning teeth in a patient jaw, the system comprising:
an attachment for bonding to a tooth at a pre-selected position, said attachment having at least one force receiving component for receiving a force; and
a polymeric shell repositioning appliance placeable over at least some of the teeth in the patient jaw, the polymeric shell having at least one force transmitting component positioned to engage the force receiving component of the attachment when the attachment at the pre-selected position and the force receiving component engage each other at contact point, wherein a position of the contact point adjusts within the locus of engagement as the tooth is repositioned.

24. The system of claim 23 wherein the locus of engagement extends over a preselected distance.

25. The system of claim 24 wherein the force receiving component and the force transmitting component are positioned so that the force transmitted to at least one tooth which lags its intended position is increased.

26. The system of claim 24 wherein the polymeric shell appliance placed over the teeth includes a cavity shaped so that a space between the appliance and the tooth permits the tooth to move into an intended position.

27. The system of claim 26 wherein the polymeric shell and attachment are shaped to permit the attachment to move relative to the appliance along a channel as the position of the contact point adjusts within the locus of engagement.

28. The system of claim 23 further comprising a pair comprising the force transmitting component and a pair comprising the force receiving component, each member of each pair being on opposing sides of the tooth.

29. The system of claim 24 wherein the range of motion is at least about 0.5 mm.

30. The system of claim 29 wherein the range of motion is at least about 1 mm.

31. The system of claim 23 wherein the force transmitting component and the force receiving component are arranged to rotate at least one of the teeth with the force.

32. The system of claim 23 wherein the force transmitting component and the force receiving component are arranged to intrude at least one of the teeth with the force.

33. The system of claim 23 wherein the force transmitting component and the force receiving component are arranged to extrude at least one of the teeth with the force.

34. The system of claim 25 wherein the position of the contact point adjusts within the locus of engagement to establish an equilibrium as the force transmitted to the at least one tooth which lags its intended position is increased.

35. The system of claim 25 wherein the force transmitting and force receiving components are arranged to counter a force from a first surface with a force from a second surface.

36. The system of claim 35 wherein the force from the first surface is an intrusive force and the force from the second surface is an extrusive force.

37. The system of claim 35 wherein the force from the first surface is an extrusive force and the force from the second surface is an intrusive force.

38. The system of claim 35 wherein a single attachment device comprises the first surface and the second surface.

39. The system of claim 35 wherein a first attachment device comprises the first surface and a second attachment device comprises the second surface.

40. The system of claim 27 wherein the force transmitting component and the force receiving component comprise a pawl and a ratchet.

41. The system of claim 40 wherein the force transmitting component comprises the ratchet and the force receiving component comprises the pawl.

42. The system of claim 40 wherein the force transmitting component comprises the pawl and the force receiving component comprises the ratchet.

43. The system of claim 27 wherein the force receiving component and the force transmitting component comprise meshing teeth.

44. A method for designing a polymeric shell tooth repositioning appliance, the method comprising:
locating an attachment on at least one tooth among several teeth of a model to define at least one force receiving component for receiving a transmitted force; and positioning an attachment receptacle to define at least one force transmitting component in a polymeric shell placeable over the teeth;

wherein the force transmitting and force receiving components are shaped to engage each other at a contact point within a locus of engagement, a position of the contact adjusting within the locus of engagement as the tooth is repositioned.

45. The method of claim 44 wherein the locus of engagement extends over a preselected distance.

46. The method of claim 44 wherein the force receiving component and the force transmitting component are positioned so that the force transmitted to at least one tooth which lags its intended position is increased.

47. The method of claim 45 wherein the polymeric shell appliance placed over the teeth includes a cavity shaped so that a space between the appliance and the tooth permits the tooth to move into an intended position.

48. The method of claim 47 wherein the polymeric shell and attachment are shaped to permit the attachment to move relative to the appliance along a channel as the position of the contact point adjusts within the locus of engagement.

49. The method of claim 44 further comprising placing a prominence at the locus of engagement for increasing the transmitted force.

50. The method of claim 44 wherein the model is a computer model and the attachment is a virtual attachment.

51. The method of claim 50 further comprising modifying the virtual attachment to form a modified virtual attachment, the modified virtual attachment for forming the attachment receptacle in the polymeric shell.

52. The method of claim 51 wherein the modifying of the virtual attachment includes modifying a position of the virtual attachment.

53. The method of claim 51 wherein the modified virtual attachment is similar to a shape of at least a portion of the virtual attachment.

54. The method of claim 53 further comprising truncating a portion of the virtual attachment.

55. The method of claim 51 wherein the modifying of the virtual attachment increases the force transmitted by the polymeric shell.

56. The method of claim 51 further comprising enhancing a surface detail during the modifying of the virtual attachment to form a modified virtual attachment with enhanced surface detail.

* * * * *